US011246987B2

(12) United States Patent
Cowe et al.

(10) Patent No.: US 11,246,987 B2
(45) Date of Patent: Feb. 15, 2022

(54) MEDICAMENT DELIVERY DEVICE

(71) Applicant: Owen Mumford Limited, Woodstock (GB)

(72) Inventors: Toby Cowe, Oxfordshire (GB); Jake Mallon, Bath (GB)

(73) Assignee: Owen Mumford Limited, Oxford (GB)

( * ) Notice: Subject to any disclaimer, the term of this patent is extended or adjusted under 35 U.S.C. 154(b) by 234 days.

(21) Appl. No.: 16/093,847

(22) PCT Filed: Apr. 27, 2017

(86) PCT No.: PCT/GB2017/051175
§ 371 (c)(1),
(2) Date: Oct. 15, 2018

(87) PCT Pub. No.: WO2017/187177
PCT Pub. Date: Nov. 2, 2017

(65) Prior Publication Data
US 2019/0151547 A1  May 23, 2019

(30) Foreign Application Priority Data

Apr. 27, 2016  (GB) .................................. 1607327

(51) Int. Cl.
*A61M 5/20* (2006.01)
*A61M 5/24* (2006.01)
*A61M 5/32* (2006.01)
*A61M 5/315* (2006.01)

(52) U.S. Cl.
CPC ........ *A61M 5/2033* (2013.01); *A61M 5/2459* (2013.01); *A61M 5/3204* (2013.01);
(Continued)

(58) Field of Classification Search
CPC ...... A61M 5/2033; A61M 2005/31518; A61M 2005/2086; A61M 2005/208;
(Continued)

(56) References Cited

U.S. PATENT DOCUMENTS

| 4,313,439 A * | 2/1982 | Babb ..................... A61M 5/172 604/28 |
| 5,300,030 A | 4/1994 | Crossman et al. |
| 2008/0188798 A1* | 8/2008 | Weber ................. A61M 5/2066 604/82 |
| 2008/0195056 A1* | 8/2008 | Bishop .................... A61M 5/42 604/218 |

FOREIGN PATENT DOCUMENTS

| EP | 2 468 337 A1 | 6/2012 |
| EP | 2 596 823 A1 | 5/2013 |
| EP | 2 698 180 A1 | 2/2014 |
| EP | 3162395 A1 * | 5/2017 .......... A61M 5/3204 |

(Continued)

OTHER PUBLICATIONS

Oct. 5, 2017 Transmittal of Int'l Search Report and Written Opinion of Int'l Searching Authority for PCT/GB2017/051175.

*Primary Examiner* — Shefali D Patel
*Assistant Examiner* — Avery Smale
(74) *Attorney, Agent, or Firm* — Quarles & Brady LLP

(57) ABSTRACT

A medicament delivery device (100) for a delivery of a medicament from a container (12) through a cannula (16). The device comprises a chassis (300), a carriage (200), and an insertion spring (70) for biasing the carriage (200) for movement in an insertion direction with respect to the chassis (300) from a starting position in which the cannula (16) is shrouded to an insertion position in which the cannula (16) is extended. A drive mechanism (400) is provided for driving a stopper (22) of the container (12) to expel the medicament. The drive mechanism (400) is carriage by the carriage (200) and comprises a movable drive member (404), a drive means (40) for applying a driving force to the drive member (404), and a force transmission means (406) for transmitting the driving force to the stopper (22). The drive means (40) is arranged around or alongside at least part of the force transmission means (406).

27 Claims, 12 Drawing Sheets

(52) U.S. Cl.
CPC ............... *A61M 2005/206* (2013.01); *A61M 2005/2006* (2013.01); *A61M 2005/208* (2013.01); *A61M 2005/2086* (2013.01); *A61M 2005/2462* (2013.01); *A61M 2005/31518* (2013.01)

(58) Field of Classification Search
CPC ...... A61M 5/31576; A61M 2005/2418; A61M 5/2459; A61M 5/3204; A61M 2005/2006; A61M 2005/2462; A61M 2005/206; A61M 5/20; A61M 2005/2073; A61M 5/31511; A61M 5/31578; A61M 5/322; A61M 2005/2013; A61M 2005/2026; A61M 5/24; A61M 5/2422; A61M 2205/8281
See application file for complete search history.

(56) References Cited

FOREIGN PATENT DOCUMENTS

| | | |
|---|---|---|
| ES | 2 365 585 | 8/2010 |
| WO | WO 02/076537 A1 | 10/2002 |
| WO | WO 03/097133 A1 | 11/2003 |
| WO | WO 2004/067068 A1 | 8/2004 |
| WO | WO-2006111861 A2 * | 10/2006 ............ A61M 5/326 |
| WO | WO 2007/002052 A2 | 1/2007 |
| WO | WO-2007002052 A2 * | 1/2007 ............. A61M 5/42 |
| WO | WO 2008/148518 A1 | 12/2008 |
| WO | WO 2009/141219 A1 | 11/2009 |
| WO | WO 2010/049239 A1 | 5/2010 |
| WO | WO 2012/025639 A1 | 3/2012 |
| WO | WO 2015/011488 A1 | 1/2015 |
| WO | WO 2016/003813 A1 | 1/2016 |

* cited by examiner

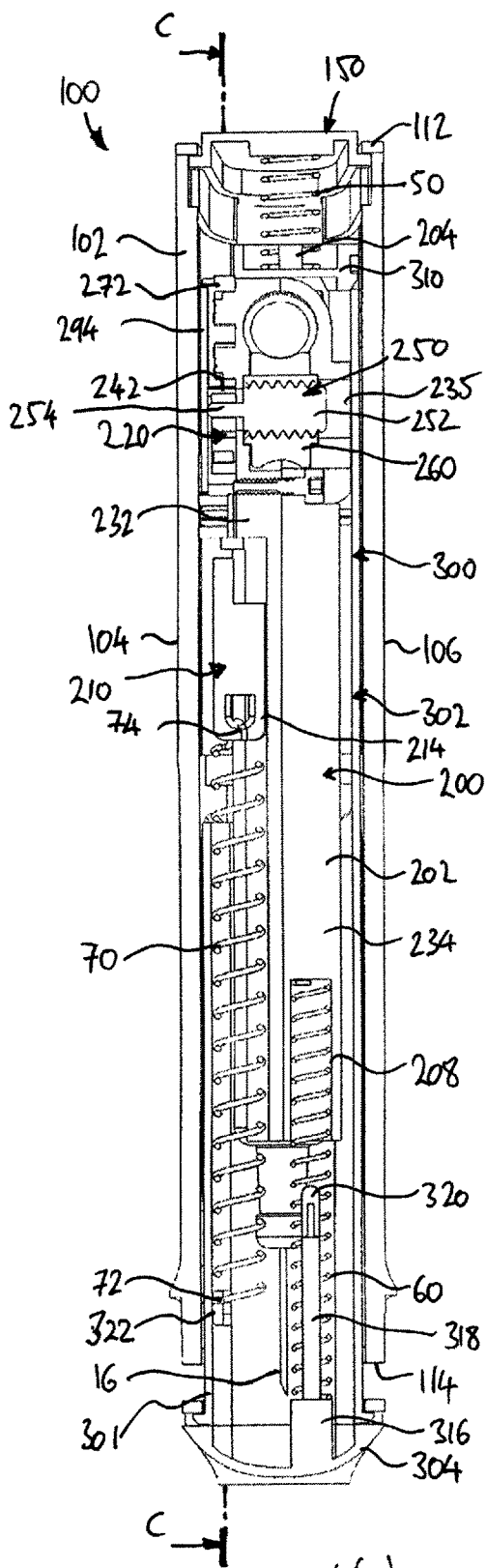
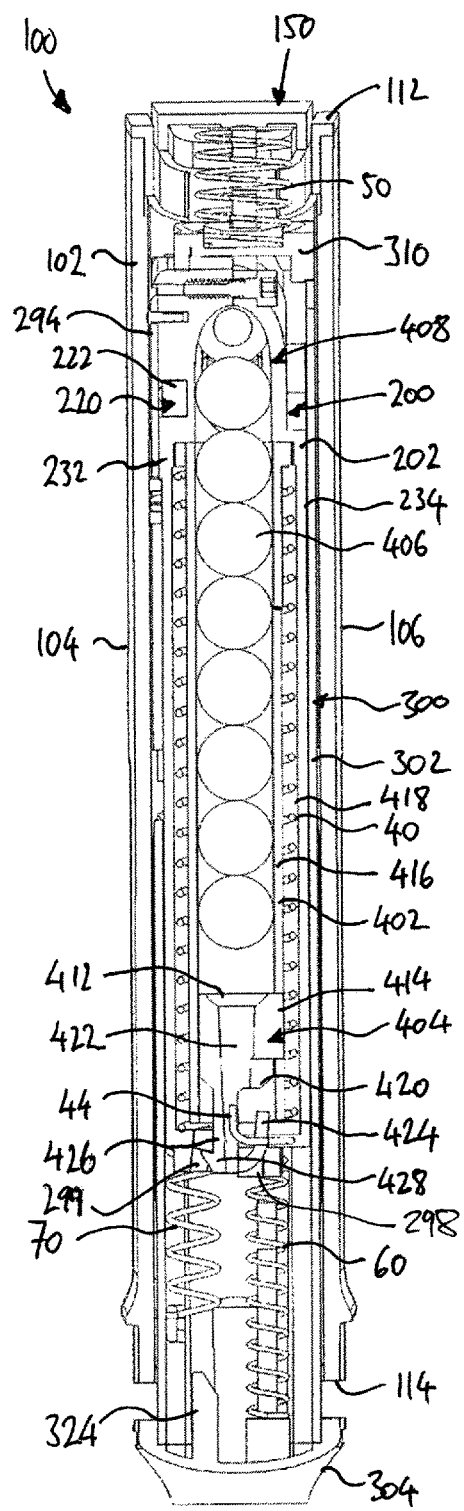
FIGURE 4(a)
(SECTION A-A)
FIGURE 4(b)
(SECTION B-B)

(SECTION C-C)

MEDICAMENT DELIVERY DEVICE

The present application is a § 371 submission of international application no. PCT/GB2017/051175, filed 27 Apr. 2017 and titled Medicament Delivery Device, which was published in the English language on 2 Nov. 2017 with publication no. WO 2017/187177 A1, and which claims the benefit of the filing date of GB 16 07327.2 filed 27 Apr. 2016, the contents of which are incorporated herein by reference.

The present invention relates to devices suitable for the delivery of a medicament to a patient. In particular, but not exclusively, the invention relates to auto-injector devices in which activation of the device causes automatic insertion of a cannula and delivery of the medicament by injection through the cannula.

Injection devices designed for automatic needle insertion and injection of a single pre-determined dose of a medicament are known in the art as auto-injectors. Such devices typically include a housing that allows the user to grip the device, a pre-filled syringe containing the medicament, and a drive mechanism. The pre-filled syringe includes a tubular glass barrel with a staked hypodermic needle at its distal end, a needle shield to protect and seal the needle, and a stopper slidably received in the barrel. One example of a pre-filled syringe of this type is available under the registered trade mark Hypak (Becton Dickinson, N.J., USA).

The syringe is axially movable within the housing between an initial, retracted position in which the needle is retracted in the housing, and a deployed position in which the needle projects from the end of the housing.

With the syringe in the retracted position, the distal end of the housing is closed by a cap. To prepare the device for use, the cap is removed. The cap is arranged to grip the rigid needle shield, so that removal of the cap pulls the rigid needle shield off the needle.

The distal end of the housing is then placed against the skin, and the user operates a trigger of the device, such as a button, to activate the drive mechanism. The drive mechanism typically comprises a plunger that is biased in the distal direction by a compression spring. The plunger is initially held in an initial, latched position by a latch arrangement. Upon activation of the drive mechanism, the plunger is released from the latched position and can move distally under the force of the compression spring.

Initially, release of the plunger causes the syringe to move from the retracted position into the deployed position, so that the needle pierces the skin. Subsequently, the plunger forces the stopper in the distal direction to inject the medicament.

Some auto-injector devices also include a needle retraction mechanism to withdraw the needle from the skin and retract it into the device once the medicament has been delivered. A needle retraction mechanism typically includes a retraction spring and a coupling arrangement for coupling the retraction spring to the syringe. Once coupled, the retraction spring applies a force to the syringe that acts in the proximal direction to move the needle back towards the retracted position. The coupling arrangement may be activated to retract the needle when the plunger nears or reaches the end of its distal travel.

Auto-injectors of these types can be convenient for self-administration by a patient of a measured dose of a medicament, although they may also be used by trained medical personnel. In both cases, auto-injectors typically offer increased user safety compared with traditional syringes, for example by ensuring that the needle used to deliver the medicament is shrouded before and/or after delivery of the medicament, and by the inclusion of interlock means or other safety devices to prevent accidental operation of the device.

However, existing auto-injector devices can have several drawbacks. For example, the above-described drive mechanism results in a relatively long device, since the plunger and the compression spring are disposed in a coaxial arrangement with the syringe. For some applications, it would be desirable to provide a more compact arrangement.

Secondly, a relatively strong drive spring is usually required to ensure delivery of the medicament through the needle. This is particularly the case when the medicament has a relatively high viscosity and/or when the needle has a fine gauge. When a powerful drive spring is also used to drive insertion of the needle, the resulting impact loads on the syringe can lead to damage of the syringe and discomfort for the patient.

Thirdly, when a needle retraction mechanism is provided, there is a risk that retraction of the needle may occur before the whole of the desired dose of medicament has been delivered. For example, variations in component dimensions due to manufacturing tolerances can give rise to variations in the point at which needle retraction is triggered, which can result in premature retraction of the needle. The relaxation of elastic strain in the device components (in particular the stopper and the plunger) can result in medicament flow through the needle even after the plunger has nominally reached the end of its stroke, resulting in a failure to deliver the complete dose if the needle is retracted too rapidly after injection. Also, if the needle is retracted before the medicament has time to dissipate into the surrounding tissue, medicament can be lost from the injection site through the puncture.

Accordingly, it would be desirable to provide an injection device that overcomes or mitigates some of the above-mentioned problems.

Against this background, in a first aspect of the present invention there is provided a medicament delivery device for the delivery of medicament from a container through a cannula, the container having a stopper for containing the medicament within the container, and the device comprising a chassis, a carriage for retaining the container and the cannula and an insertion spring for biasing the carriage for movement in an insertion direction with respect to the chassis from a starting position in which the cannula is shrouded to an insertion position in which the cannula is extended. The device further comprises a drive mechanism for driving the stopper along a container axis to expel medicament through the cannula upon activation of the drive mechanism. The drive mechanism is carried by the carriage and comprises a drive member that is movable with respect to the carriage, a drive means for applying a driving force to the drive member along a drive axis, and force transmission means for transmitting the driving force from the drive member to the stopper. The drive means is arranged around or alongside at least part of the force transmission means and comprises a tension spring.

By providing a drive means comprising a tension spring, and by accommodating the drive means around or alongside at least a part of the force transmission means, a compact arrangement can be achieved.

With this arrangement, the tension spring can extend away from the drive member in the same direction as the driving force. In comparison, in prior art arrangements in which a compression spring is used, the spring extends away from the drive member in a direction opposite to the driving force, so that an additional space is required to accommodate the drive spring behind the drive member.

Furthermore, because the drive arrangement, the container and the cannula are carried by the carriage, the driving force acts only within the carriage and not on any other part of the device. Accordingly, a relatively powerful drive means can be used without increasing patient discomfort or increasing the risk of damage to the device. In addition, because a separate insertion spring is provided to drive the insertion movement of the carriage, the insertion spring can be selected such that a reliable yet comfortable cannula insertion force is applied, without regard to the force required to expel the medicament. Furthermore, with this arrangement, the noise made by the device at the start of the injection sequence can be reduced compared to prior art arrangements.

In one embodiment, the tension spring is arranged concentrically around at least a part of the force transmission means. This leads to a particularly compact arrangement. The drive means may comprise a first end coupled to the drive member and a second end coupled to the carriage, in which case the force transmission means is preferably disposed at least partly between the first and second ends of the drive means.

The drive axis need not be coaxial with the container axis. For example, the drive axis may be parallel to and spaced from the container axis. In one particularly compact arrangement, the drive means is disposed alongside the container. The cannula is preferably an injection needle, such as a hypodermic needle. Conveniently, the container comprises a pre-filled syringe. The force transmission means may be non-linear to re-direct the force of the drive means in such arrangements. In general terms, a first end of the force transmission means may be aligned with the drive axis, and a second end of the force transmission means may be aligned with the container axis.

In one example, the force transmission means comprises an array of balls, such as ball bearings. With this arrangement, the force transmission means can be shaped along any required route in the carriage but without any substantial change in the length of the force transmission means under load, for example due to elastic deformation or flexing.

The force transmission means may be guided in a guide track associated with the carriage. In some arrangements, such as when the drive means is disposed alongside the container, the guide track may include a U-shaped part to allow the force transmission means to reverse the direction of the driving force. A part of the force transmission means may be received or receivable in the container. For example, when the force transmission means comprises an array of balls, the balls may have a diameter sized to fit within the container for cooperation with the stopper.

The drive mechanism may comprise a guide element for guiding movement of the drive member along the drive axis. The tension spring may be arranged concentrically around the guide element, such that the guide element also serves as a guide for the tension spring. When a guide track is provided, the guide track may be defined in part by the guide element, so that the guide element also guides the force transmission means. The guide element may be generally tubular. In one embodiment, the drive member comprises a guide formation for cooperation with a slot in the guide element to prevent turning movement of the drive member. When the drive mechanism is operated, the tension spring may pass through the slot.

A shock absorber may be disposed between the drive member and the stopper, to reduce impact loads on the container on operation of the drive mechanism. For example, the shock absorber may be disposed between the force transmission means and the stopper. The shock absorber may be of an elastomeric foam material.

The drive mechanism may be activated in response to the carriage reaching an activation position during movement of the carriage towards the insertion position. In this way, the drive mechanism can be automatically activated once the carriage has moved to insert the cannula in the injection site. Advantageously, medicament delivery does not begin before the cannula has pierced the skin, thus avoiding wastage of medicament or spillage of medicament onto the skin. The activation position may be intermediate the starting position and the insertion position of the carriage, so that activation of the drive mechanism is triggered before the end of movement of the carriage. Alternatively, the activation position may substantially correspond to the insertion position. A drive trigger may be provided for activating the drive mechanism when the carriage reaches the activation position. The drive trigger may be associated with the chassis.

The drive mechanism may comprise a drive latch for latching the drive member in an initial position, and the drive trigger may be arranged to cooperate with the drive latch when the carriage reaches the activation position to release the drive member for movement along the drive axis. A latch stop may be associated with the carriage, and the drive latch may be arranged to engage with the latch stop to hold the drive member in the initial position. To avoid unintentional release of the drive mechanism, spring means may be provided for biasing the drive latch into engagement with the latch stop.

The device may include a carriage latch arrangement for holding the carriage in the starting position and for allowing movement of the carriage in the insertion direction under the bias of the insertion spring upon release of the carriage latch arrangement. The device may comprise a trigger component operable to release the carriage latch arrangement. When the carriage is in the insertion position, the cannula may extend through an aperture in the chassis.

The device may include an interlock member that is movable with respect to the chassis to switch the device from a neutral state in which release of the carriage latch arrangement is not possible to a ready state in which the trigger button is operable to release the carriage latch arrangement. An interlock spring may be provided for biasing the interlock member and the chassis apart, and the interlock member may be movable with respect to the chassis against the bias of the interlock spring to switch the device from the neutral state to the ready state. In one embodiment, the interlock member comprises a housing body for retaining the trigger component. When present, the interlock spring may bias the trigger component away from the chassis. The device may comprise a removable cap for closing an end of the chassis, in which case the cap may be arranged to block movement of the interlock member with respect to the chassis when the cap is fitted to the device. In this way, the device cannot be switched to the ready state until the cap has been removed.

The insertion spring is preferably disposed parallel to and spaced from both the drive axis and the container axis. In this way, the insertion spring can be accommodated in a compact arrangement without increasing the length of the device. The insertion spring may comprise a tension spring.

The device may further comprise a coupling mechanism for releasably coupling the insertion spring to the carriage. The drive mechanism may be arranged to activate the coupling mechanism to cause decoupling of the insertion spring from the carriage after delivery of the medicament, thereby to allow movement of the carriage away from the insertion position. A retraction spring may be provided for driving movement of the carriage away from the insertion position to retract the cannula after delivery of the medicament.

The provision of a retraction spring in combination with a releasable coupling for the insertion spring provides a means for automatic retraction of the cannula from the injection site once the dose of medicament has been delivered.

To this end, and from a second aspect, the invention resides in a medicament delivery device for the delivery of medicament from a container through a cannula, the container having a stopper for containing the medicament within the container, and the device comprising a chassis, a carriage for retaining the container and the cannula, an insertion spring for biasing the carriage for movement in an insertion direction with respect to the chassis from a starting position in which the cannula is shrouded to an insertion position in which the cannula is extended, a coupling mechanism for releasably coupling the insertion spring to the carriage, a drive mechanism operable to move the stopper along a container axis to expel medicament through the cannula, and a retraction spring for biasing the carriage in a retraction direction, opposite to the insertion direction. The drive mechanism is arranged to activate the coupling mechanism, and activation of the coupling mechanism causes decoupling of the insertion spring from the carriage, thereby to allow movement of the carriage in the retraction direction under the bias of the retraction spring after delivery of the medicament.

With this arrangement, a simple and compact device capable of automatic cannula insertion and cannula retraction can be provided. In particular, because movement of the carriage in the retraction direction is caused by decoupling of the insertion spring from the carriage, the retraction spring can be simply located between the chassis and the carriage without the need for a further coupling arrangement. Neither the insertion spring nor the retraction spring are involved in the delivery of the medicament using the drive mechanism, and therefore each spring can be selected to optimise its role. The drive mechanism may be carried by the carriage, so that the forces involved in operation of the drive mechanism are not transferred to the patient through the chassis.

The coupling mechanism preferably comprises a coupling member that is moveable with respect to the carriage upon activation of the coupling mechanism to decouple the insertion spring from the carriage. The device may comprise retaining means for preventing movement of the coupling member with respect to the carriage. The retaining means may be arranged to release the coupling member, thereby to activate the coupling mechanism. Said another way, release of the coupling member by the retaining means triggers the start of the operation of the coupling mechanism.

The retaining means may be arranged to release the coupling member in response to operation of the drive mechanism. For example, the retaining means may comprise a retaining element for engagement with the coupling member, and the retaining element may be movable with respect to the carriage in response to operation of the drive mechanism to disengage from the coupling member. The retaining element may disengage from the coupling member when the drive mechanism has moved the stopper through a pre-defined distance. In this way, activation of the coupling mechanism occurs at the appropriate point during the operating sequence of the device. Movement of the retaining element may be perpendicular to the insertion direction, to provide a compact arrangement.

In one embodiment, the device comprises a wheel driven by the drive mechanism, and the retaining element is in threaded engagement with the wheel. In this way, turning movement of the wheel causes disengagement of the retaining element from the coupling member.

The drive mechanism may comprise a drive member, drive means for applying a driving force to the drive member along a drive axis, and force transmission means for transmitting the driving force from the drive member to the stopper, and the wheel may be driven by the force transmission means. The drive axis may be parallel to the container axis, and the force transmission means may be guided in a U-shape around the wheel. This provides a particularly compact arrangement.

Preferably, the retaining element disengages from the coupling member upon turning movement of the wheel through a pre-determined angle. In this way, the point in the operating sequence at which the coupling mechanism is activated can be accurately determined.

The device may further comprise an actuator for driving movement of the coupling member. The actuator is preferably arranged to apply a force to the coupling member to bias the coupling member for movement. In one embodiment, the coupling member is guided for lateral movement with respect to the insertion direction, and the actuator is arranged to apply a lateral force to the coupling member. The device may comprise actuator drive means for applying a force to the actuator to drive movement of the coupling member. In one example, the actuator drive means comprises a constant force spring.

The actuator may comprise a crank having a crank lever for driving movement of the coupling member. The crank may be driven to turn under the influence of the actuator drive means. The carriage may comprise a hub for the crank.

The device may comprise a link member connected to the insertion spring. For example, the link member may be arranged to engage with a termination of the insertion spring. The link member may be releasably engaged with the coupling member to couple the insertion spring to the carriage, in which case movement of the coupling member with respect to the carriage may cause disengagement of the link member from the coupling member to decouple the insertion spring from the carriage.

In one arrangement, the link member comprises an engagement formation for engagement with a corresponding engagement formation of the coupling member, and movement of the coupling member upon activation of the coupling mechanism causes disengagement of the engagement formations. The engagement formations may be shaped so that movement of the coupling member through a predetermined distance is required before the engagement formations disengage.

The carriage may comprise guide means for guiding movement of the link member parallel to the insertion direction upon decoupling of the insertion spring from the carriage. The guide means prevents the decoupled insertion spring from fouling other components in the device. In one example, the guide means comprises a slot for receiving a clip of the link member.

Optionally, decoupling of the insertion spring from the carriage occurs substantially immediately after activation of the coupling mechanism. Preferably, however, the device is arranged such that the insertion spring is decoupled from the carriage after a delay time has elapsed following activation of the coupling mechanism. By providing a delay time, the coupling mechanism can be activated before the end of a delivery stroke of the stopper, whilst the drive mechanism is still operational, yet allows the cannula to remain inserted in the injection site until after the end of the delivery stroke.

Activation of the coupling mechanism before the end of the delivery stroke is advantageous, since this relaxes the tolerances required to ensure correct operation of the device. At the same time, preventing premature retraction of the cannula helps to ensure that the whole dose of medicament is injected. Furthermore, the delay time can be such that the cannula remains in the insertion position for enough time after the end of the delivery stroke to allow dissipation and absorption of the medicament into the injection site.

In one embodiment, the device comprises damping means for retarding movement of the coupling member after activation of the coupling mechanism. By retarding or slowing the movement of the coupling member, the time taken for the coupling member to move far enough to trigger decoupling of the insertion spring is increased. Preferably, the damping means comprises a viscous damper. The damping means may comprise a rotary damper, which provides a compact and reliable time delay means for the device.

Conveniently, when the device includes an actuator comprising a crank mounted on a hub, the hub may comprise a chamber of the rotary damper, and the crank may comprise a vane of the rotary damper.

The device may comprise a carriage latch arrangement for holding the carriage in the starting position and for allowing movement of the carriage in the insertion direction under the bias of the insertion spring upon release of the carriage latch arrangement. The device may further comprise a trigger component, such as a button, that is operable to release the carriage latch arrangement. In this way, the trigger component is operable to start the sequence of steps in the operation of the device, including cannula insertion, medicament delivery and cannula retraction, through a single user action. The cannula may comprise an injection needle, in particular a hypodermic needle, and the container may comprise a pre-filled syringe.

Preferably, the device is arranged so that the chance of accidental operation is reduced. To that end, the device may comprise an interlock member that is movable with respect to the chassis to switch the device from a neutral state in which release of the carriage latch arrangement is not possible to a ready state in which the trigger button is operable to release the carriage latch arrangement. The interlock member may be arranged to move with respect to the chassis to switch the device to the ready state when the device is placed against an injection site. For example, the interlock member may comprise a housing body for retaining the trigger component. An interlock spring may be provided for biasing the interlock member and the chassis apart. The device may comprise a removable cap for closing an end of the chassis, in which case the cap may be arranged to block movement of the interlock member with respect to the chassis when the cap is fitted to the device. In this way, the device cannot be switched to the ready state until the cap has been removed.

The insertion spring is preferably coupled to the chassis. For example, an end termination of the insertion spring may be engageable in an aperture in a body of the chassis. The insertion spring is preferably a tension spring. The retraction spring may be a compression spring. The carriage may comprise a recess for receiving the retraction spring, thus helping to accommodate the length of the retraction spring without increasing the overall length of the device.

The chassis may comprise a carriage stop for stopping movement of the carriage when the carriage reaches the insertion position. The carriage stop may comprise a cushion for damping movement of the carriage upon impact with the carriage stop. This helps to avoid high impact loads being transmitted to the patient as the carriage moves to the insertion position, prevents the carriage bouncing to ensure a single clean insertion is achieved, and reduces the sound generated during operation of the device. Conveniently, the retraction spring may be guided by the carriage stop.

In a third aspect, the present invention provides a medicament delivery device for the delivery of medicament from a container through cannula, the container having a stopper for containing the medicament within the container, the device comprising a chassis, a carriage for retaining the container and the cannula, an insertion mechanism operable to apply an insertion force to the carriage to move the carriage in an insertion direction with respect to the chassis from a starting position in which the cannula is shrouded to an insertion position in which the cannula is extended, and a drive mechanism operable to move the stopper through a delivery stroke in the container to expel medicament through the cannula. The device further comprises a retraction mechanism for moving the carriage in a retraction direction opposite to the insertion direction and arranged for activation by the drive mechanism, and a time delay mechanism for providing a delay time between the end of the delivery stroke and the movement of the carriage in the retraction direction.

The provision of the time delay mechanism helps to prevent premature retraction of the cannula. In this way, complete delivery of the desired dose of medicament can be achieved. The cannula may be an injection needle, in particular a hypodermic needle, and the container may comprise a pre-filled syringe.

The retraction mechanism may comprise a releasable coupling for removing the insertion force from the carriage to allow movement of the carriage in the retraction direction. The time delay mechanism may act to delay the release of the coupling following activation of the retraction mechanism. The coupling may comprise a coupling member that is movable with respect to the carriage to release the coupling, and the retraction mechanism may further comprise an actuator for moving the coupling member upon activation of the retraction mechanism.

An actuator drive means may be provided for applying a force to the actuator to drive movement of the coupling member, and the time delay mechanism may comprise a damper for retarding movement of the actuator under the influence of the actuator drive force, thereby to delay release of the coupling. The actuator drive means may comprise a constant force spring.

The actuator may comprise a crank having a crank lever for driving movement of the coupling member. In this case, the damper may comprise a chamber defined by a hub of the crank and containing a viscous fluid, and a vane received in the chamber and movable with the crank. Movement of the vane in the chamber, and hence movement of the crank, is damped by the viscous fluid.

In another embodiment, the actuator may be omitted, and a coupling drive means may be provided for applying a force directly to the coupling member. In this case, the time delay mechanism may comprise a damper that acts directly on the coupling member to retard movement of the coupling member.

The device may comprise activation means for activating the retraction mechanism. The activation means may be driven by the drive mechanism. The time delay mechanism preferably provides a delay time between activation of the retraction mechanism and movement of the carriage in the retraction direction. To avoid the risk of the retraction mechanism failing to activate, for example due to an unfavourable combination of manufacturing tolerances, the activation means may be arranged to activate the retraction mechanism before the end of the delivery stroke.

When a coupling member is provided, the activation means may comprise a retaining element for preventing movement of the coupling member with respect to the carriage. The retaining element may be movable to allow movement of the coupling member upon activation of the retraction mechanism. In one embodiment, the retaining element is in threaded engagement with a wheel and the wheel is driven by the drive mechanism to move the retaining element to release the coupling member.

The drive mechanism may comprise a drive member that is movable with respect to the carriage, driving means for applying a driving force to the drive member, and force transmission means for transmitting the driving force from the drive member to the stopper. Conveniently, the wheel may be driven by the force transmission means.

The insertion mechanism may comprise an insertion spring for applying the insertion force to the carriage. The insertion spring is preferably a tension spring. The retraction mechanism may comprise a retraction spring for applying a retraction force to the carriage.

Any suitable time delay mechanism may be used, but in one particularly preferred example, the time delay mechanism comprises a rotary damper.

The insertion mechanism may comprise a carriage latch arrangement for holding the carriage in the starting position and for allowing movement of the carriage in the insertion direction upon release of the carriage latch arrangement. A trigger component operable to release the carriage latch arrangement may be provided.

To reduce the risk of unintentional operation of the device, an interlock member that is movable with respect to the chassis to switch the device from a neutral state in which release of the carriage latch arrangement is not possible to a ready state in which the trigger button is operable to release the carriage latch arrangement. The interlock member may comprise a housing body for retaining the trigger component. An interlock spring may be provided for biasing the interlock member and the chassis apart, and the interlock member may be movable with respect to the chassis against the bias of the interlock spring to switch the device to the ready state. The device may comprise a removable cap for closing an end of the chassis, in which case the cap may be arranged to block movement of the interlock member with respect to the chassis when the cap is fitted to the device. In this way, the device cannot be switched to the ready state until the cap has been removed.

Preferred and/or optional features of each aspect of the invention may also be used, alone or in appropriate combination, in the other aspects of the invention also.

Embodiments of the present invention will now be described, by way of example only, with reference to the accompanying drawings, in which like reference numerals are used for like features, and in which.

Figure 1:
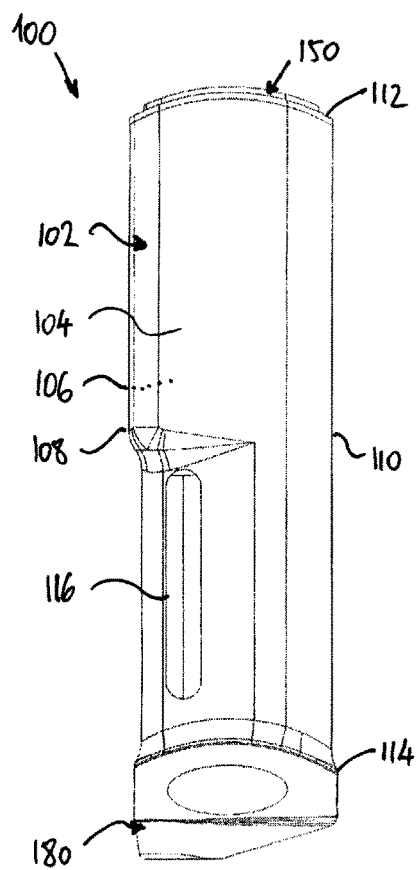
FIG. 1 is a side view of a device according to the present invention.
Figure 3:
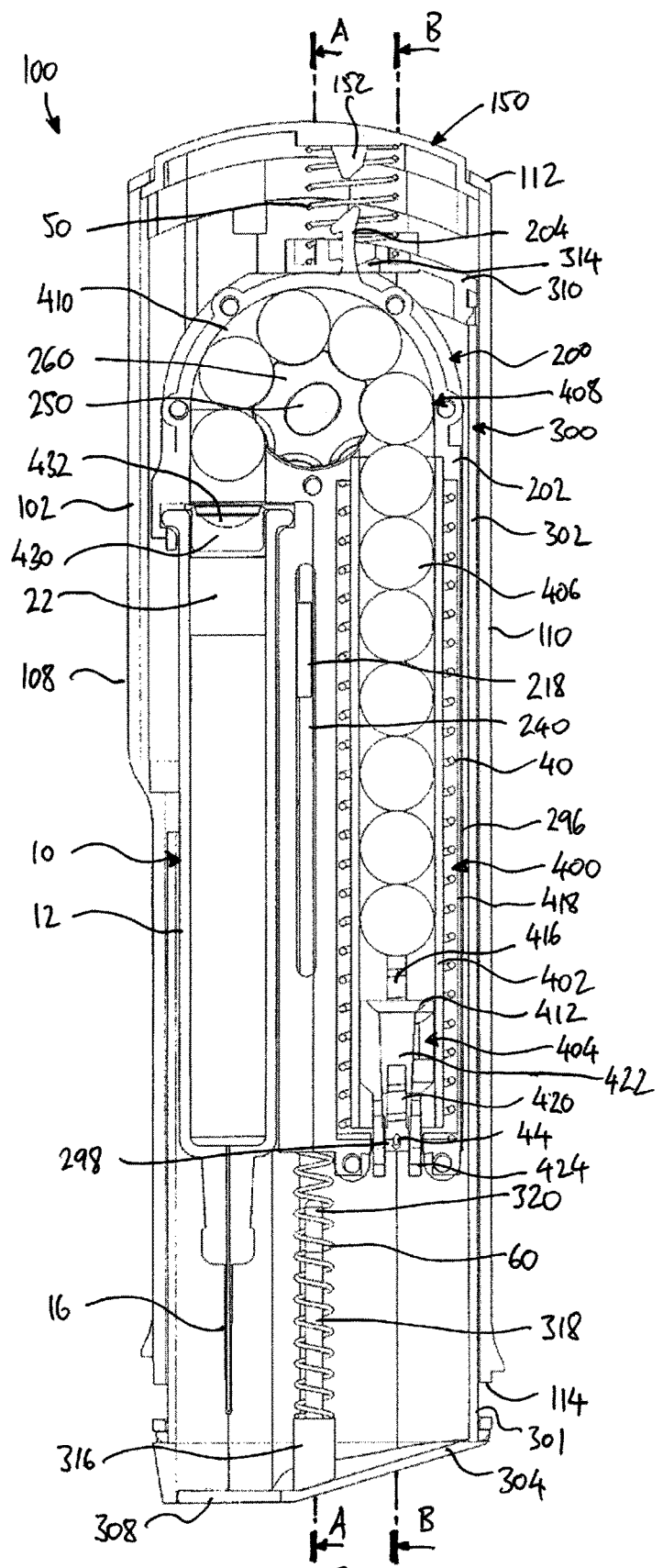
FIG. 3 is a further cross-sectional view of the device of FIG. 1, with a cap removed.
Figure 5:
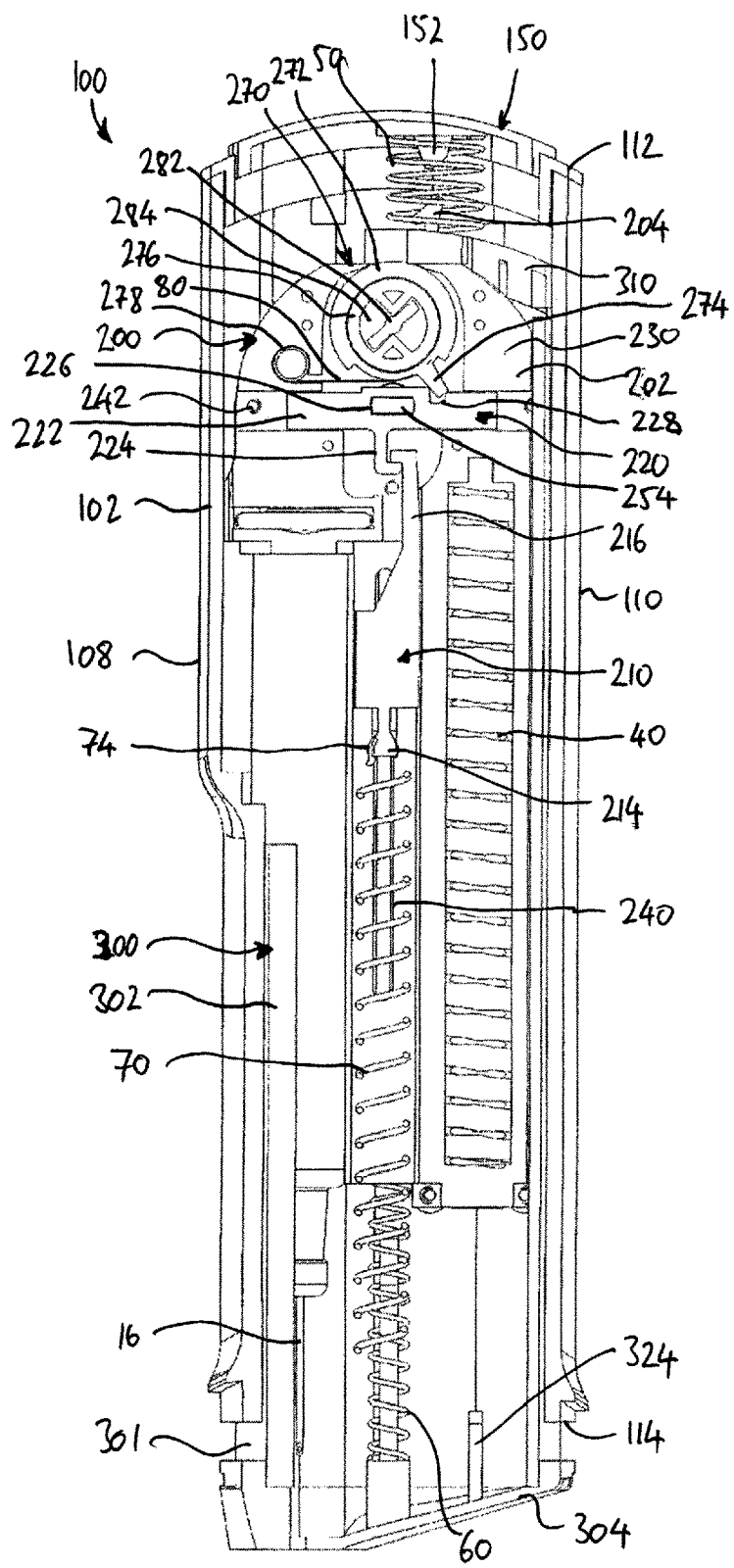
Figure 7:
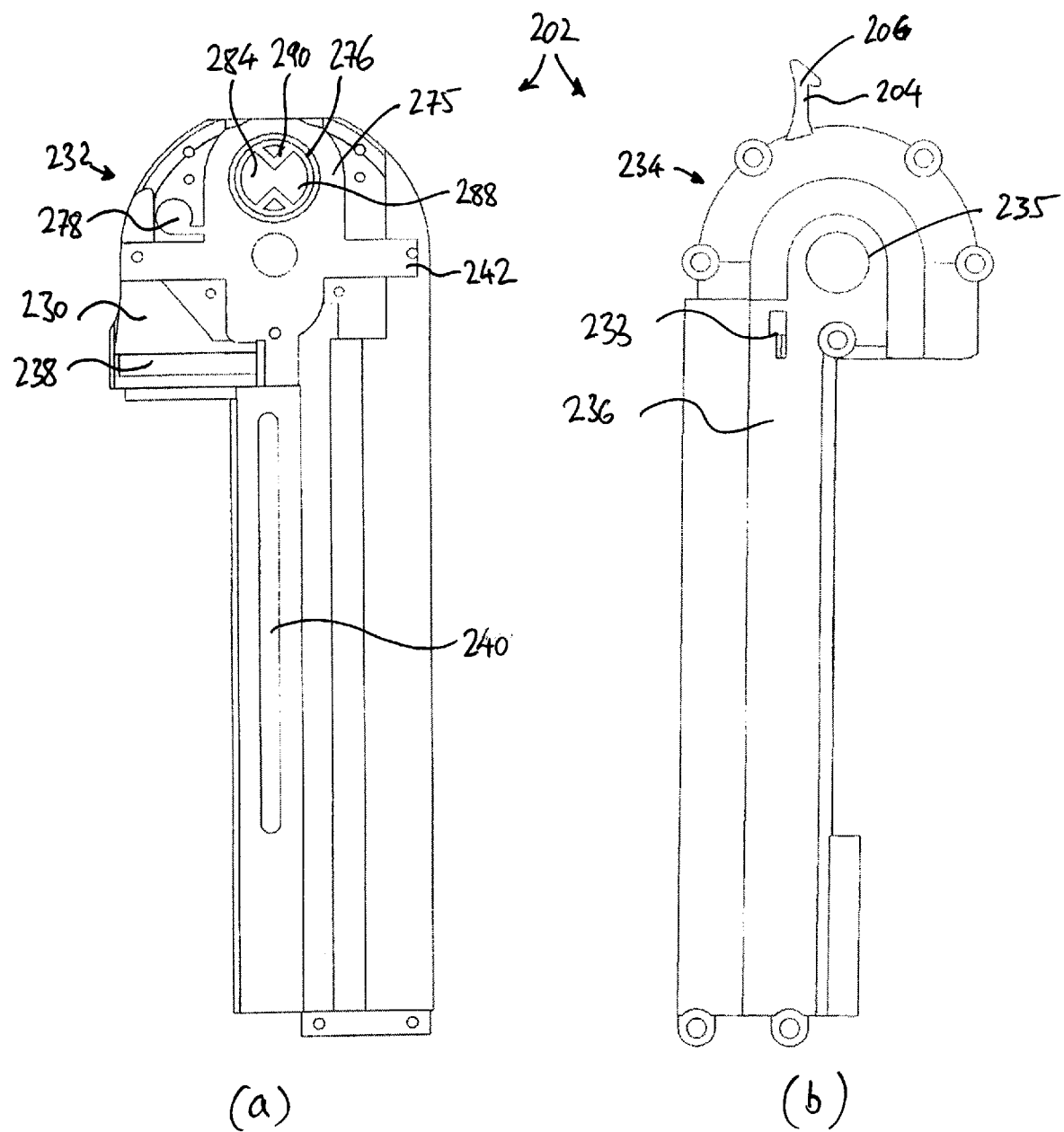

FIGS. 4(a) and 4(b) are sectional views taken on planes A-A and B-B in FIG. 3, respectively;

FIG. 5 is a sectional view taken on plane C-C in FIG. 4(a);

FIGS. 6(a) and 6(b) show an insertion spring and associated components of the device of FIG. 1;

FIGS. 7(a) and 7(b) show front and rear carriage body components, respectively, of the device of FIG. 1;

FIGS. 8(a) to 8(f) are schematic illustrations of needle insertion and medicament delivery steps in an operating sequence of the device of FIG. 1;

FIGS. 9(a) to 9(d) are schematic illustrations of needle retraction steps in the operating sequence of the device of FIG. 1;

FIGS. 10(a) and 10(b) are cross-sectional views of part of a device according to a second embodiment of the invention; and FIGS. 11(a) and 11(b) are cross-sectional views of part of a device according to a third embodiment of the invention.

Throughout the following description, the term "distal" and related terms are used to refer to the end of the device that is towards the patient's skin in use (i.e. the lower end of the device in FIG. 1), and the term "proximal" and related terms are used to refer to the end of the device that is furthest from the skin in use (i.e. the upper end of the device in FIG. 1). The term "front" and related terms are used to refer to the face of the device that is visible in FIG. 1 and to the left in FIGS. 4(a) and 4(b), and the term "rear" and related terms are used to refer to the opposite face of the device that is not visible in FIG. 1 and to the right in FIGS. 4(a) and 4(b).

Figure 2:
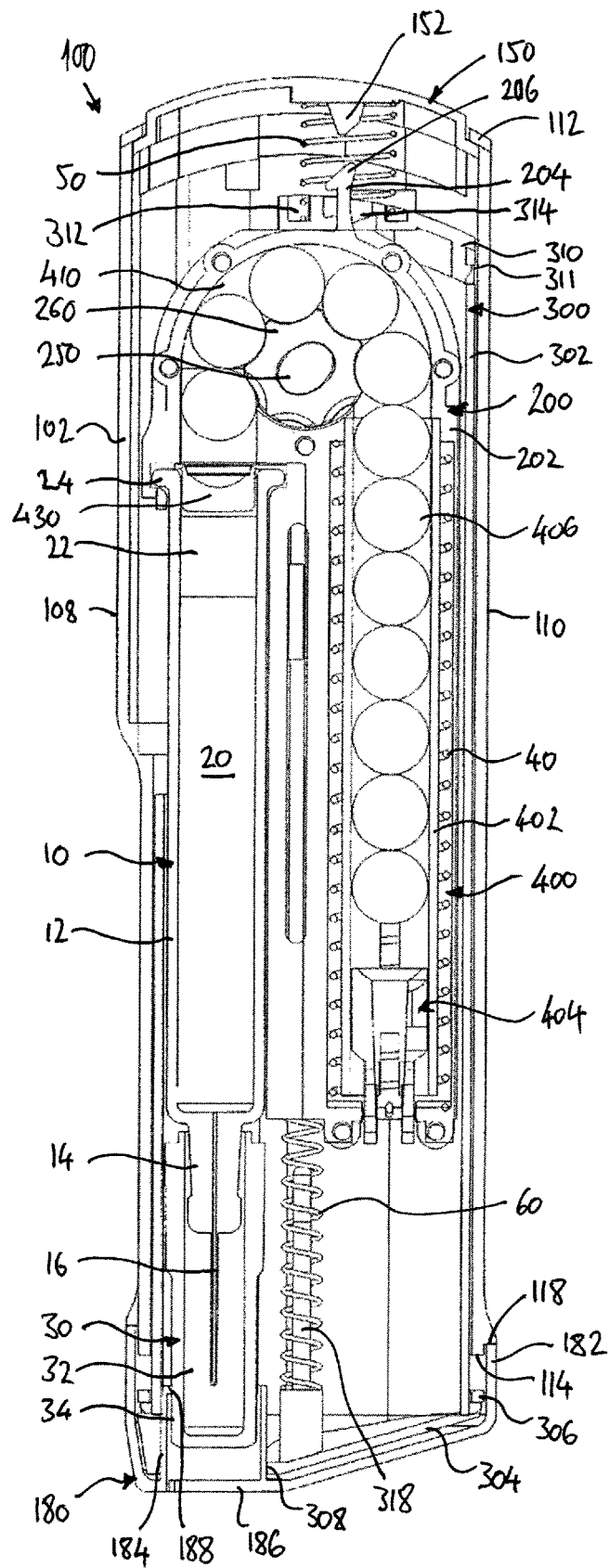
FIG. 2 is a cross-sectional view of the device of FIG. 1 on an enlarged scale.

Referring first to FIGS. 1 and 2, a device 100 according to the invention comprises an elongate housing body 102 having a flattened cross-section to define front and rear faces 104, 106 and left and right hand side faces 108, 110. A trigger button 150 is retained in the proximal end 112 of the housing body 102. The distal end 114 of the housing body 102 is closed by a removable deshielder cap 180.

As shown in FIG. 2, the housing body 102 contains a medicament container in the form of a pre-filled syringe 10. The syringe 10 comprises a generally tubular glass body or barrel 12 that defines a container axis. At its distal end, the barrel 12 is formed into a reduced-diameter end portion 14 that carries a staked cannula in the form of a hypodermic needle 16. The barrel 12 is filled with a quantity of medicament 20 and is closed by a stopper 22 that is slidably received in the barrel 12. An outwardly-projecting flange 24 is provided at the proximal end of the barrel 12.

In an initial state of the device 100, a removable needle shield 30, comprising an elastomeric insert 32 and a rigid cap 34 and known in the art as a rigid needle shield, is attached to the distal end portion 14 of the barrel 12, to seal the needle 16 and prevent leakage of the medicament 20 from the container. The syringe 10 may be of a type generally known in the art, for example as available under the registered trade mark Hypak (Becton Dickinson, N.J., USA). A window 116 in the housing body 102 (see FIG. 1) allows part of the syringe barrel 12 to be viewed from outside the device 100.

Referring again to FIG. 2, the syringe 10 is retained in the housing body 102 by a carriage 200. The carriage 200 is slidably mounted in a chassis 300 that, in turn, is slidably mounted in the housing body 102. As will be explained in more detail below, the carriage 200 comprises a carriage body 202 and houses a drive mechanism 400 of the device, which includes a drive means in the form of a tension spring 40 that is mounted generally parallel to and alongside the syringe barrel 12.

The chassis 300 comprises a hollow body 302 that is closed at its distal end by a cover piece 304. The cover piece 304 is attached to the chassis body 302 by clips 306. The chassis body 302 is transparent so as not to obstruct the view of the syringe barrel 12 through the window 116 (not shown in FIG. 2). The cover piece 304 is opaque and comprises an aperture 308 that is aligned with the axis of the syringe barrel 12. As shown most clearly in FIG. 2, the deshielder cap 180 is arranged to fit over the distal end 114 of the housing body 102 to conceal the cover piece 304 of the chassis 300. When fitted, an outer wall 182 of the cap 180 abuts a ridge 118 formed on the housing body 102, to block movement of the housing body 102 with respect to the chassis 300. A tubular internal wall 184 of the cap 180 extends proximally from a base part 186 of the cap 180 and through the aperture 308 in the cover piece 304 to engage with the needle shield 30. The internal wall 184 is provided with barbs 188 to grip the cap 34 of the needle shield 30.

The proximal end of the chassis body 302 is attached to a carriage stay 310 that extends generally laterally within the housing body 102 and is disposed between the carriage 200 and the trigger button 150. The carriage stay 310 is engaged with the chassis body 302 by way of clips 311. An interlock spring 50 is disposed between the carriage stay 310 and the underside (i.e. the distal side) of the trigger button 150 and acts in compression to bias the trigger button 150 and the chassis 300 apart. The proximal face of the carriage stay 310 is shaped to define an annular spring seat 312 for the interlock spring 50.

The spring seat 312 is disposed around an aperture 314 that extends through the carriage stay 310 to accept a hook 204 provided on the proximal end of the carriage body 202. The hook 204 extends through the aperture 314 so that a head formation 206 of the hook 204 engages with the proximal side of the carriage stay 310, adjacent to the aperture 314. Thus the hook 204 and the carriage stay 310 form a latch arrangement for the carriage 200. As will be explained below, a ramped trigger pin 152 extends distally from the underside of the trigger button 150 to cooperate with the hook 204 during the operating sequence of the device 100.

The deshielder cap 180 can be removed from the housing body 102 by pulling the deshielder cap 180 in the distal direction. The barbs 188 on the internal wall 184 of the cap 180 pull the needle shield 30 off the syringe 10, so that the needle shield 30 is withdrawn through the aperture 308 in the cover piece 304 as the cap 180 is removed. Distal movement of the chassis 300 with respect to the housing body 102 is limited by abutment between respective stops (not shown) formed on the chassis body 302 and the housing body 102. In turn, distal movement of the carriage 200 with respect to the chassis 300 is limited by engagement of the hook 204 on the carriage body 202 with the carriage stay 310 of the chassis 300. In this way, the carriage 200, and hence the syringe 10, remain substantially fixed in position with respect to the housing body 102 upon removal of the deshielder cap 180.

FIGS. 3 to 5 show the device 100 with the deshielder cap 180 removed. Referring first to FIGS. 3 and 4(a), a compression spring, referred to hereafter as a retraction spring 60, is provided to bias the carriage 200 in the proximal direction with respect to the chassis 300. As shown most clearly in FIG. 4(a), the carriage body 202 comprises a blind bore 208 for receiving the proximal end of the retraction spring 60. The distal end of the retraction spring 60 is seated on a cylindrical spring seat 316 formed on the proximal side of the cover piece 304. A rod-like spring guide 318 extends proximally from the spring seat 316 towards the blind bore 208. The tip of the spring guide 318 carries a cushioning piece 320 formed from an elastomeric foam material, such as a polyurethane foam.

Referring to FIGS. 4(a) and 5, a further spring, referred to hereafter as an insertion spring 70, acts in the opposite direction to the retraction spring 60 to bias the carriage 200 in the distal direction with respect to the chassis 300.

The insertion spring 70 is a tension spring with hooked end terminations 72, 74. The distal end termination 72 of the insertion spring 70 is hooked through a hole 322 in the chassis body 302 (see FIG. 4(a)). The proximal end termination 74 of the insertion spring 70 is releasably coupled to the carriage body 202 by way of a spring coupling or link member 210 and a coupling member, referred to hereafter as a slider 220. Referring additionally to FIGS. 6(a) and 6(b), which show the interlock spring 70 and associated components from the rear and front sides, respectively, the link member 210 has a generally cylindrical body 212 with a loop 214 at its distal end, an elongate, L-shaped hook 216 at its proximal end and a guide clip 218 that projects rearwardly from the body 212. The slider 220 comprises a laterally-extending bar 222, and an L-shaped hook 224 is disposed on the distal side of the slider 220 to engage with the hook 216 of the link member 210. The proximal end termination 74 of the insertion spring 70 is hooked through the loop 214 in the link member 210.

The slider 220 and the link member 210 are mounted on a front face 230 of the carriage body 202. The carriage body 202 is a two-part clamshell assembly, with front and rear carriage body parts 232, 234 as shown in isolation in FIGS. 7(a) and 7(b). FIG. 7(a) shows the front face 230 of the front carriage body part 232, and FIG. 7(b) shows the rear face 236 of the rear carriage body part 234. Both carriage body parts 232, 234 are cut away on their respective left hand sides (when viewed from the front of the device) to accommodate the syringe barrel 12. The front carriage body part 232 also includes a lateral slot 238 to retain the flange 24 of the syringe 10, so that the syringe 10, including the barrel 12 and the needle 16, remains coupled to and fixed in position with respect to the carriage 200 throughout the operation of the device 100.

Referring to FIG. 7(a), the front carriage body part 232 further includes a longitudinally-extending slot 240 that is disposed alongside and parallel to the syringe barrel 12. The slot 240 receives the guide clip 218 of the link member 210. The guide clip 218 thus cooperates with the slot 240 to attach the link member 210 to the front carriage body 232, whilst allowing the link member 210 to slide longitudinally along the front face 230 of the carriage 200.

The slider 220 is accommodated in a laterally-extending channel 242 formed in the front face 230 of the front carriage body part 232. The channel 242 is perpendicular to the longitudinal axis of the device 100 and parallel to the front face 104 of the housing body 102. The channel 242 guides the slider 220 for lateral movement with respect to the carriage 200, but prevents distal movement of the slider 220 with respect to the carriage 200. In this way, when the link member 210 is engaged with the slider 220, by engagement of the respective hooks 216, 224, the load of the insertion spring 70 is transferred to the carriage 200.

Lateral movement of the slider 220 is initially prevented by a retaining pin 250. Referring back to FIG. 4(a), the retaining pin 250 extends orthogonally with respect to both the longitudinal axis of the device 100 and the lateral slider channel 242. The retaining pin 250 has a threaded body 252 and an end tab 254 for engagement with the slider 220. The slider 220 includes an aperture 226 for receiving the end tab 254.

As shown most clearly in FIGS. 3, 4(a) and 6(a), the body 252 of the retaining pin 250 is in threaded engagement with a wheel or sprocket 260, which is housed in the carriage body 202. In the initial state of the device 100, the retaining pin 250 is positioned so that the end tab 254 is engaged in the aperture 226 of the slider 220, to lock the slider 220 against lateral movement in the channel 242. As will be explained in more detail below, rotation of the sprocket 260 during operation of the device 100 causes the retaining pin 250 to move towards the rear face 106 of the housing body 102, withdrawing the end tab 254 from the aperture 226 and releasing the slider 220 for lateral movement with respect to the carriage 200.

Referring now to FIGS. 5, 6(a) and 6(b), an actuator in the form of a crank assembly 270 is provided to drive lateral movement of the slider 220. The crank assembly 270 comprises a crank ring 272 having a crank lever 274 that projects radially from the crank ring 272. The crank ring 272 is disposed in a recess 275 in the front face 230 of the front carriage body 232 to lie in substantially the same plane as the slider 220. The recess 275 is shaped to define a ring-shaped hub 276 (see also FIG. 7(a)), upon which the crank ring 272 is rotatably mounted.

A constant force spring 80 is provided to apply a torque to the crank ring 272 that urges the crank ring 272 to turn in a clockwise direction around the hub 276 (when viewed as in FIG. 5). One end of the constant force spring 80 is attached to the crank ring 272. The other end of the constant force spring 80 is wound into a spring recess 278 in the front face 230 of the front carriage body 232. In the initial state of the device 100, the crank ring 272 is positioned such that the crank lever 274 engages with a slot 228 in the proximal side of the slider 220.

Referring to FIG. 7(a), the front side of the crank ring 272 is closed by a cover disc 280. The rear side of the cover disc 280 carries a rotor or vane formation 282 that projects into a chamber 284 formed by the interior of the hub 276 on the front face 230 of the front carriage body 232. The vane formation 282 is shaped to define two radially-extending bars 284 connected at the centre of the cover disc 280 by a cylindrical boss 286. As shown in FIG. 7(a), the chamber 284 is partly divided into two sectors 288 by a pair of triangular lands 290 that extend radially from the hub 276 towards the centre of the chamber 284. When assembled, the boss 286 of the vane formation 282 is accommodated between the lands 290, and each one of the bars 284 of the vane formation 282 is disposed within a respective one of the sectors 288 of the chamber 284. The chamber 284 is filled with a viscous fluid, such as a silicone grease. In this way, when the crank ring 272 turns during the operating sequence of the device 100 under the influence of the constant force spring 80, as will be described in more detail below, the vane formation 282 displaces the fluid in the chamber 284 to provide a viscous damping of the movement of the crank ring 272.

A cover plate 294, most clearly visible in FIGS. 4(a) and 4(b), is attached to the front face 230 of the front carriage body 232 to retain the slider 220 and the crank ring 272 on the hub 276.

Referring again to FIGS. 3 and 4(b), the drive mechanism 400 of the device 100, with the drive spring 40, is accommodated principally in the right hand side of the carriage 200. The drive mechanism 400 includes a guide tube 402, a piston member 404 that is slidably received in the guide tube 402, and a force transmission means comprising a plurality of balls 406 arranged in a linear array along a J-shaped guide track 408.

The guide track 408 is defined in part by the front and rear carriage body parts 232, 234 and in part by the guide tube 402. The guide tube 402 is received in a cylindrical cavity 296 that extends within the right hand side of the carriage 200. The guide tube 402 accommodates several of the balls 406 and defines a long linear portion of the guide track 408. The carriage body parts 232, 234 are shaped to define a U-shaped part 410 of the guide track 408 that extends from the proximal end of the cylindrical cavity 296 and around the sprocket 260. The left hand end of the U-shaped part 410 of the guide track 408 opens into the bore of the syringe barrel 12 on the left-hand side of the carriage 200 to define the remainder of the guide track 408. The balls 406 are sized to fit within the bore of the syringe barrel 12.

The piston member 404 is received in the distal end of the guide tube 402 and comprises a proximal face 412 that is cup-shaped for cooperation with the closest one of the balls 406. A longitudinally-extending rib 414 is provided on the rear side of the piston member 404. The guide tube 402 includes a longitudinally-extending slit 416 to receive the rib 414, so that the piston member 404 can slide within the guide tube 402 without rotating about the axis of the guide tube 402.

The piston member 404 is biased in the proximal direction by the drive spring 40. The drive spring 40 comprises a helical tension spring with hooked end terminations and is accommodated concentrically around the linear portion of the guide track 408, in the space 418 between the guide tube 404 and the cylindrical cavity 296 in the carriage body 202. In this way, the guide tube 404 also acts as a spring guide for the drive spring 40. The proximal end termination (not visible) of the drive spring 40 is hooked into an aperture 233 in the rear carriage body 232 (see FIG. 7(b)). The distal end termination 44 of the drive spring 40 passes through a slot 420 in the rear side of the piston member 404 to locate in a frustoconical bore 422 of the piston member 404. In the initial state of the device, the drive spring 40 is stretched along its length to store energy and, as will be described in more detail below, is arranged to apply a linear force to the piston member 404 along a drive axis when released.

Referring to FIG. 4(b), at its distal end, the piston member 404 is provided with a pair of spring fingers 424 disposed on either side of the slot 420 on the rear side of the piston member 404, and a latch formation 426 that extends along the front side of the piston member 404. With the device 100 in the initial state, the latch formation 426 extends through an aperture 298 in the distal end of the carriage body 202. The latch formation 426 has a hook-shaped head 428 arranged to releasably engage with a stop 299 formed on the front carriage body 232 at the front side of the aperture 298. At the same time, the spring fingers 424 press against the rear side of the aperture 298 to brace the latch formation 426 in engagement with the stop 299 on the front carriage body 232. Thus the latch formation 426 prevents proximal movement of the piston member 404 under the influence of the drive spring 40 when the head 428 is engaged with the front carriage body 232.

A firing pin 324 with a ramped proximal end extends proximally from the cover piece 304 of the chassis 300. As will be explained in more detail below, the firing pin 324 is shaped to cooperate with the latch formation 426 to release the piston member 404 for proximal movement during the operating sequence of the device 100.

Turning back to FIG. 3, a shock absorber cup 430 is received in the barrel 12 of the syringe 10, on the proximal side of the stopper 22. The proximal face 432 of the shock absorber cup 430 is shaped to cooperate with the closest one of the balls 406. The shock absorber cup 430 is of a plastics foam material, for example a polyurethane foam, to cushion the impact between the balls 406 and the stopper 22 upon activation of the drive mechanism 400. The balls 406 are arranged along the guide track 408 to form a chain or array. The periphery of the sprocket 260 is shaped to cooperate with the balls 406 in the adjacent track 408, so that movement of the balls 406 along the guide track 408 turns the sprocket 260.

In the illustrated device 100, the ball 406 at the distal end of the array on the right side of the guide track 408 is spaced from the proximal face 412 of the piston member 404 and the ball 406 at the distal end of the array on the left side of the guide track 408 is spaced from the proximal face 432 of the shock absorber cup 430, although it will be appreciated that the balls 406 are not attached to one another and that the spacing of the balls 406 may differ in practice. In preferred arrangements, smaller clearances than those shown are present between the respective proximal contact faces 412, 432 and the corresponding balls 406. It is also possible for the proximal contact faces 412, 432 to be in contact with the corresponding balls 406, in which case the shock absorber cup 430 can deform to take up any difference in length between the array of balls 406 and the distance between the proximal faces 412, 432 when the components are in their initial positions.

Figure 8:
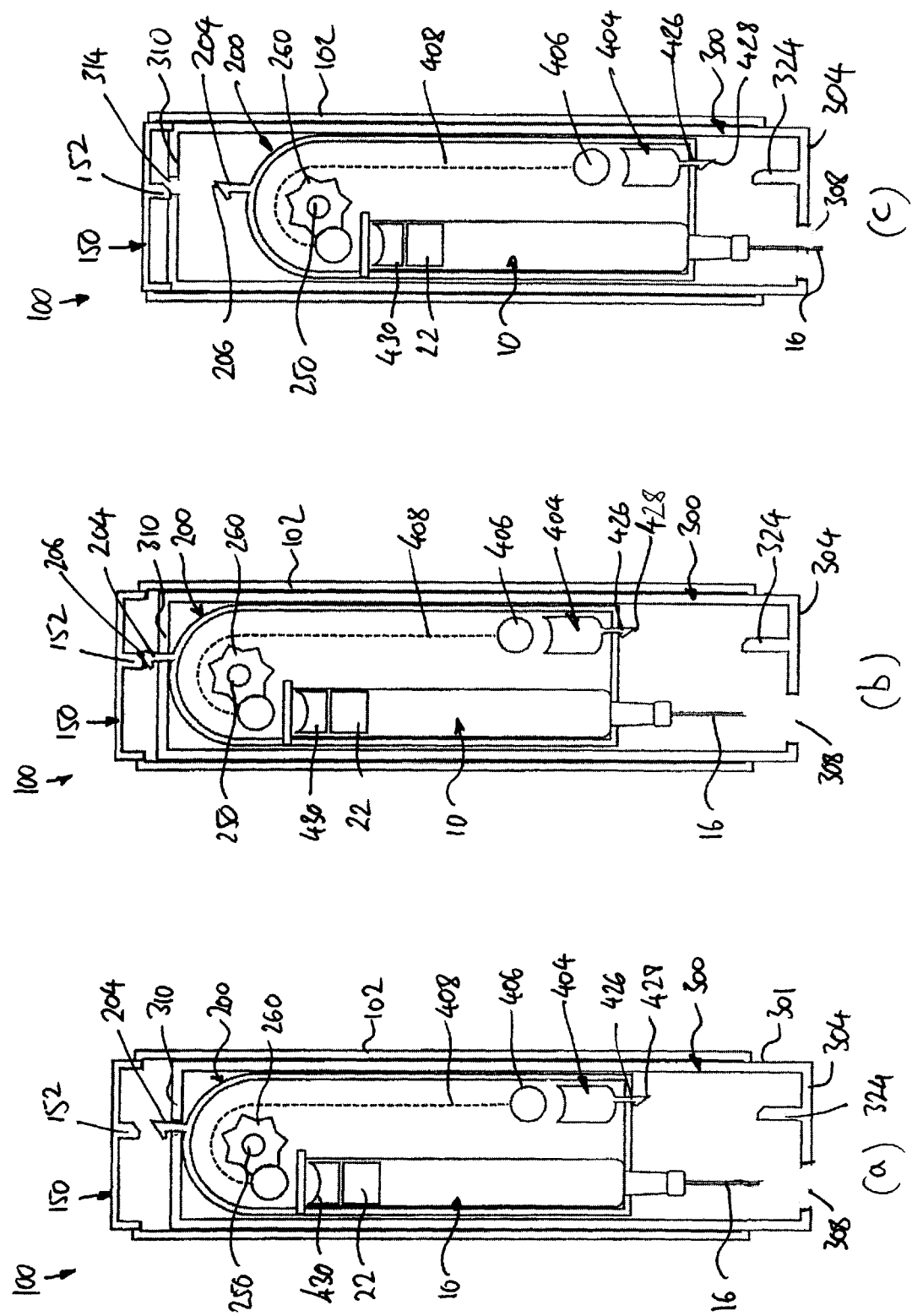
Figure 8:
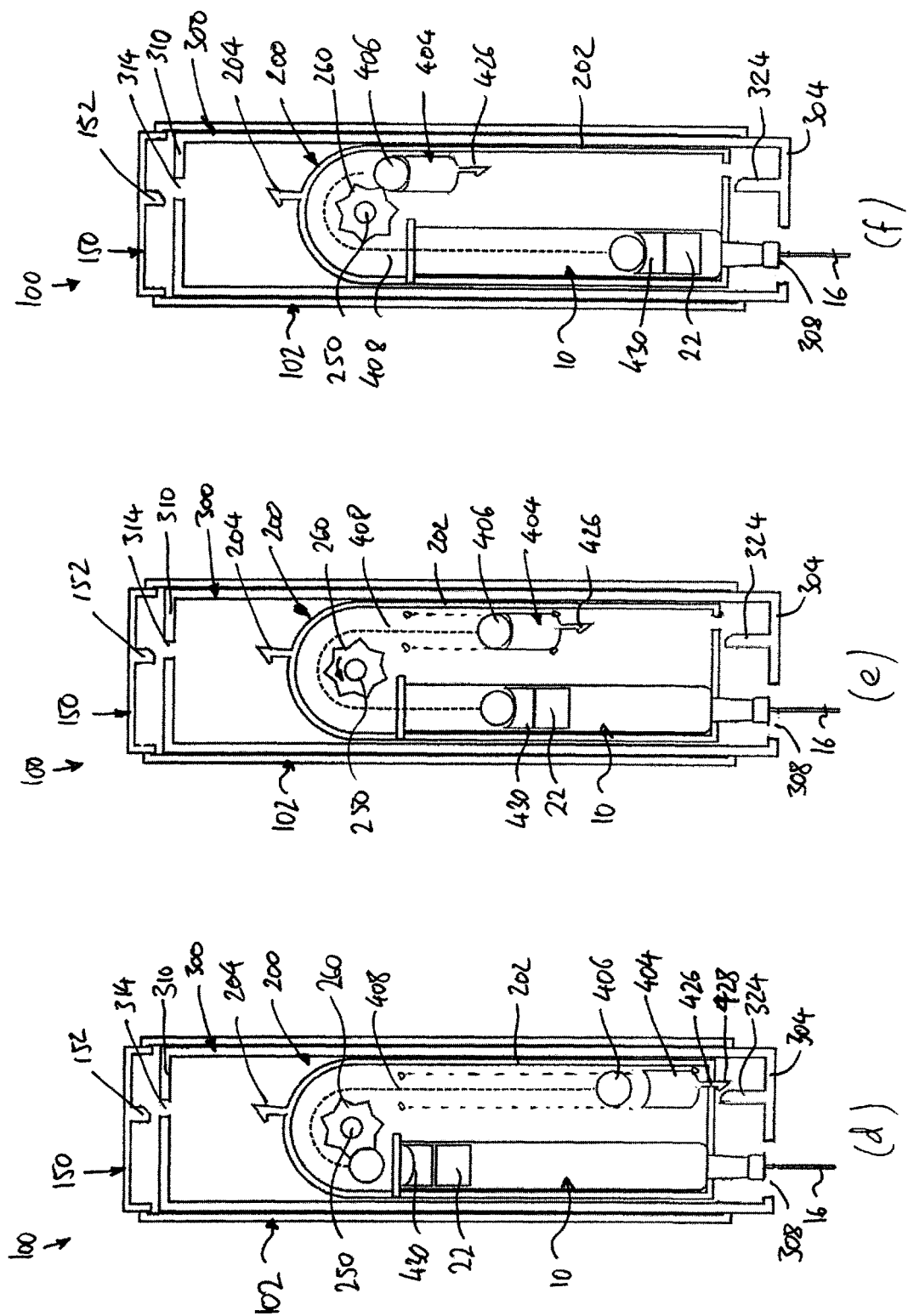

The operating sequence of the device 100 will now be described. FIG. 8 provides simplified schematic illustrations of the device 100 at various operational stages, in which many of the parts are omitted and in which the position and orientation of some components has been altered for clarity. FIG. 8 shows cross-sections of the device taken on the same plane as in FIG. 3.

First, referring to FIGS. 3, 4, 5 and 8(a), after removal of the deshielder cap, a distal end portion 301 of the chassis body 302, which carries the cover piece 304, protrudes from the distal end 114 of the housing body 102, and the trigger button 150 protrudes from the proximal end 112 of the housing body 102. In this way, the housing body 102, the chassis 300 and the trigger button 150 together define an enclosed casing of the device 100. Engagement of the hook 206 with the carriage stay 310 holds the carriage 200 a starting position with respect to the chassis 300, such that the needle 16 shrouded within the device 100.

With the cap 180 removed, the housing body 102 and the chassis 300 can now move relative to one another. The interlock spring 50 (not shown in FIG. 8) acts between the trigger button 150 and the carriage stay 310 of the chassis 300 so that both the chassis 300 and the trigger button 150 are biased to return to their original positions in the event that either component is pushed into the housing body 102 and then released.

The spacing between the trigger button 150 and the carriage stay 310 of the chassis 300 is such that, when the chassis 300 is in its initial, distally-protruding position, the trigger pin 152 of the trigger button 150 does not reach the hook 204 of the carriage 200 if the trigger button 150 is depressed. In this state, the device 100 can be said to be in a neutral state in which accidental operation of the device 100 is prevented.

To prepare the device 100 for operation, the user holds the housing body 102 and presses the cover piece 304 of the chassis 300 against the injection site. This causes the housing body 102 to move distally with respect to the chassis 300 and the carriage 200, as shown in FIG. 8(b).

The distal displacement of the housing body 102, and hence the trigger button 150, with respect to the chassis 300 causes the trigger pin 152 of the trigger button 150 to move closer to the hook 204 of the carriage 200. In this way, the housing body 102 acts as an interlock member or interlock sleeve for the device, and displacement of the housing body 102 in the distal direction causes the device 100 to switch from the neutral state to a ready state. With the device in the ready state, the trigger button 150 can be depressed (i.e. moved distally with respect to the housing body 102) so that the trigger pin 152 contacts the hook 204. The trigger pin 152 has a ramped shape so that movement of the trigger pin 152 against the hook 204 delatches the head part 206 of the hook 204 from the carriage stay 310, allowing the hook 204 to pass through the aperture 314 in the carriage stay 310.

Once the hook 204 has been released from the carriage stay 310, the carriage 200 moves distally with respect to the chassis 300 and the housing body 102 into an insertion position, as shown in FIG. 8(c). The distal movement of the carriage 200 is driven by the insertion spring (not shown in FIG. 8), which is coupled to the carriage body 202 by the link member 210 and the slider 220, as described above with reference to FIG. 5.

Distal movement of the carriage 200 causes the needle 16 of the syringe 10 to extend out of the device 100 through the aperture 308 in the cover piece 304 to pierce the skin at the injection site. As the carriage 200 moves distally, the retraction spring 60 (see FIG. 4(a), not shown in FIG. 8) is compressed and the spring guide 318 moves into the bore 208 in the carriage body 202. Distal movement of the carriage 200 stops when the cushioning piece 320 reaches the blind end of the bore 208. In this way, the spring guide 318 acts as a stop for the carriage, and the length of the spring guide 318 defines the insertion position of the carriage 200 and thus sets the insertion depth of the needle 16. The cushioning piece 320 deforms upon contact with the end of the bore 208 to reduce the impact load as the carriage 200 reaches the end of its travel.

It will be appreciated that the insertion spring 70, the trigger button 150, the hook 204 and the carriage stay 310 together define an insertion mechanism of the device 100 that is operable to apply an insertion force to the carriage 200 to move the carriage 200 the distal direction with respect to the chassis from a starting position in which the needle 16 is shrouded to an insertion position in which the needle 16 is extended.

Towards the end of the distal movement of the carriage 200, the carriage 200 reaches an activation position in which the firing pin 324 on the cover piece 304 of the chassis 300 comes into contact with the head 428 of the latch formation 426 on the piston member 404 (see FIG. 8(d)). The firing pin 324 is shaped to displace the latch formation 426 towards the rear face of the device 100, bending the spring fingers 424 (see FIG. 4(b), thereby to cause the latch formation 426 to disengage from the stop 299 on the carriage body 202. In this way, the drive mechanism 400 of the device 100 is activated, and proximal movement of the piston member 404 under the load of the drive spring (not shown in FIG. 8) can now take place. The drive spring applies a linear driving force to the piston member 404 to urge the piston member 404 along a drive axis defined by the guide tube 402. The drive axis runs parallel to and is spaced from the axis of the container.

As the piston member 404 moves proximally within the guide tube 402 (see FIGS. 4(b) and 5, not shown in FIG. 8), the piston member 404 pushes the balls 406 around the guide track 408 and into the syringe barrel 12, as shown in FIG. 8(e). The load of the drive spring is thus transferred through the array of balls 406 to the distal ball on the left side of the guide track 408, which contacts the shock absorber cup 430. In turn, the shock absorber cup 430 pushes the stopper 22 of the syringe 10 distally to expel medicament through the needle 16. The shock absorber cup 430 reduces the risk of impact damage to the syringe 10 and reduces the impact sound.

Proximal movement of the piston member 404 continues until the rib 414 on the piston member 404 reaches the end of the slit 416 in the guide tube 402 (see FIG. 4(b)). At this point, shown in FIG. 8(f), distal movement of the stopper 22 of the syringe 10 ceases and medicament delivery ends.

Referring again to FIGS. 3 and 4(a), the movement of the balls 406 along the guide track 408 during medicament delivery turns the sprocket 260 in an anticlockwise direction (when viewed as in FIG. 3). Cooperation between the end tab 254 of the retaining pin 250 and the slot 226 prevents rotation of the retaining pin 250 as the sprocket 260 turns. As a result, threaded engagement between the sprocket 260 and the retaining pin 250 causes the retaining pin 250 to move rearwardly into a recess 235 in the rear carriage housing part 234 (visible in FIG. 7(b)). This causes the end tab 254 of the retaining pin 250 gradually to withdraw from the slot 226 in the slider 220.

The end tab 254 of the retaining pin 250 moves clear of the slider 220 before the end of the proximal movement of the piston member 404. In this way, it is ensured that the slider 220 will always be released for lateral movement before movement of the piston member 404 ends, even accounting for manufacturing tolerances and the like. In one example, the end tab 254 of the retaining pin 250 is withdrawn from the slider 220 when the piston member 404 is approximately 1 mm from the end of its travel in the proximal direction. As will be explained in more detail below, withdrawal of the retaining pin 250 from the slider 220 activates the next stage of operation of the device, which culminates in withdrawal of the needle 16.

Figure 6:
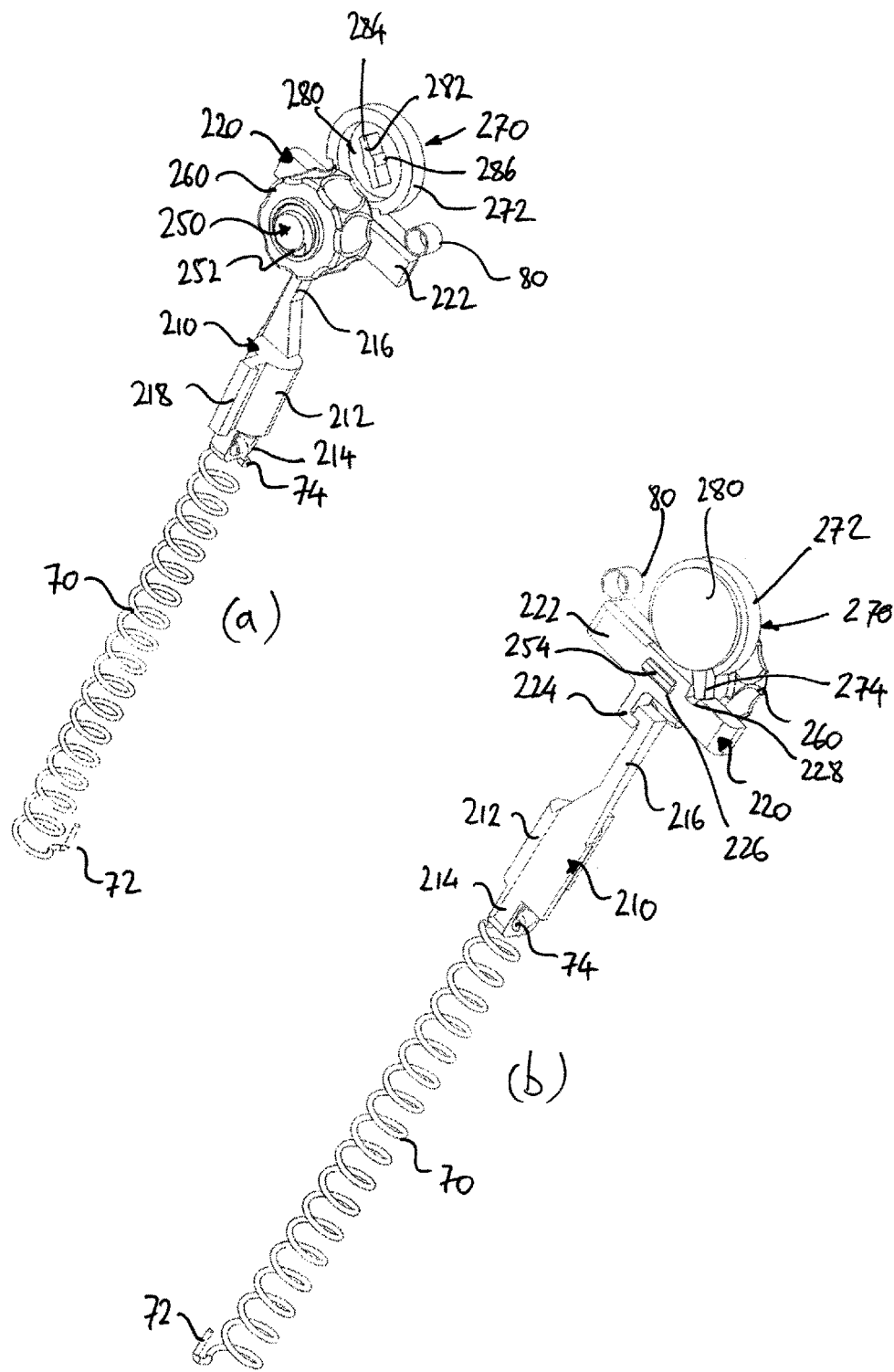
Figure 9:
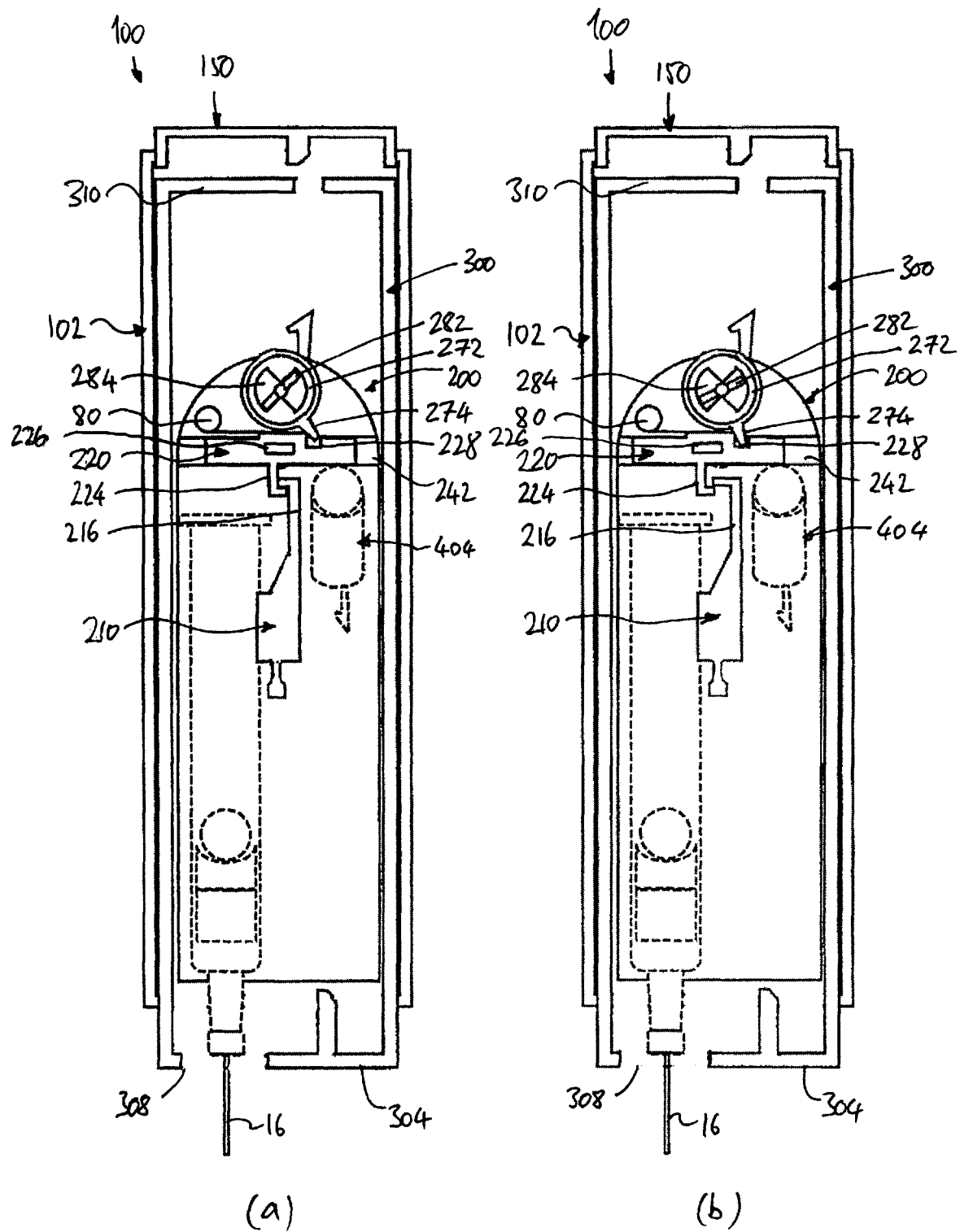
Figure 9:
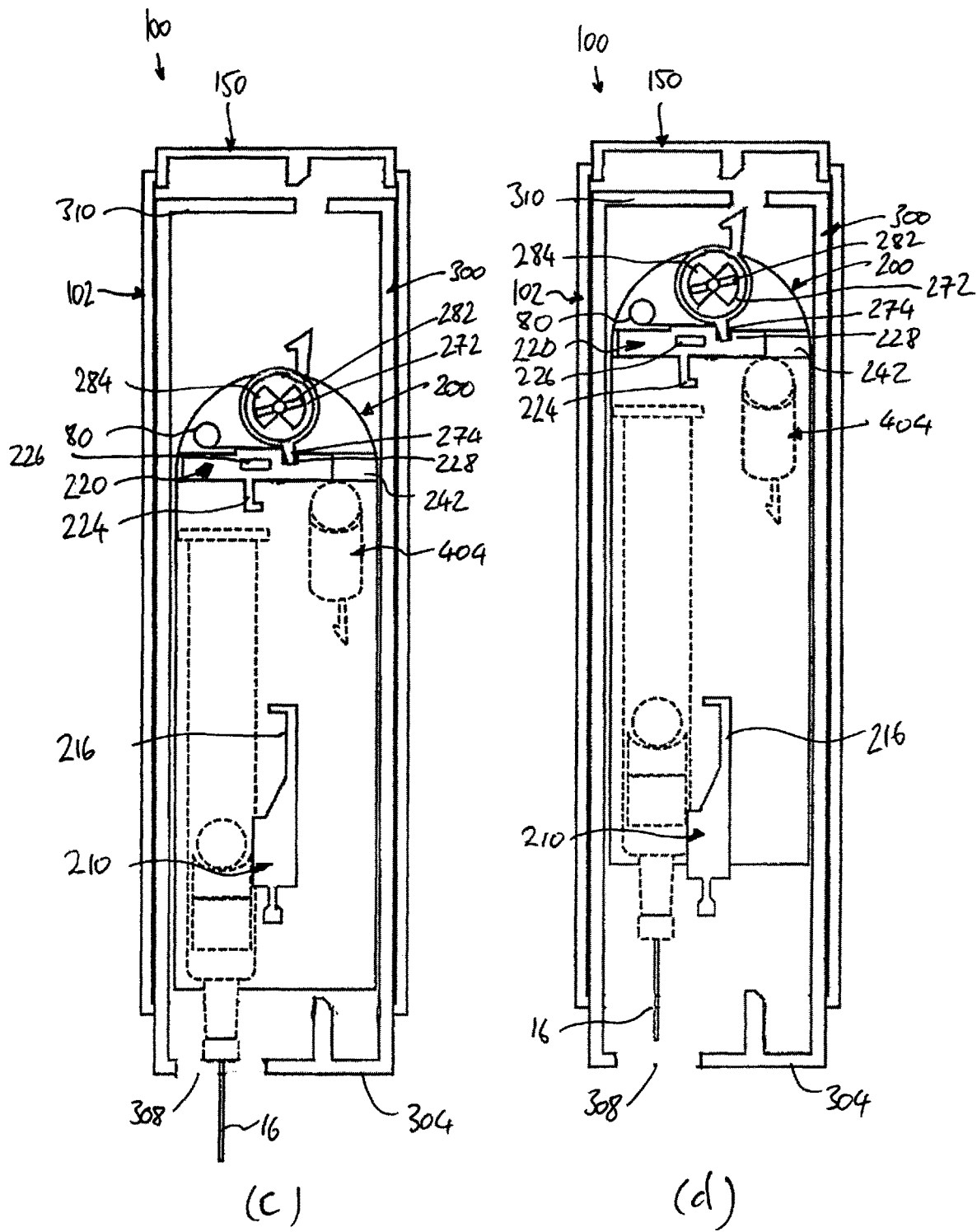

The next part of the operating sequence will be described with reference to FIGS. 4(a), 5 and 6, and also to FIG. 9, which provides further simplified schematic illustrations of the device 100 at various operational stages. As in FIG. 8, in FIG. 9 many of the parts are omitted and in which the position and orientation of some components has been altered for clarity. FIG. 9 shows cross-sections of the device taken on the same plane as in FIG. 5.

FIG. 9(a) shows the device 100 towards the end of medicament delivery, when the piston member 404 has almost reached the end of its travel and when the end tab 254 of the retaining pin 250 has been withdrawn from the slider 220. The slider 220 is now able to move laterally within the channel 242. The slider 220 is driven to move to the left by the crank lever 274 as the crank ring 272 turns under the torque applied by the constant force spring 80. However, the turning speed of the crank ring 272 is restricted by the viscous damping that arises as the vane formation 282 moves through the viscous fluid in the chamber 284. As a result, lateral movement of the slider 220 is retarded and occurs slower than would be the case if no viscous damping were provided.

As shown in FIGS. 9(b) and 9(c), as the slider 220 moves to the left, the respective hooks 216, 224 of the link member 210 and the slider 220 disengage from one another, releasing the link member 210 from the slider 220 and thus decoupling the insertion spring 70 from the carriage 200. Once released, the link member 210 moves distally with respect to the carriage 200 as the tension in the insertion spring 70 (not shown in FIG. 9) relaxes.

After disengagement of the link member 210, the carriage 200 is no longer biased distally by the insertion spring 70. The compressed retraction spring 60 (see FIGS. 4(a) and 5) now causes the carriage 200 to move in the proximal direction, resulting in retraction of the needle 16 from the injection site.

The time delay between withdrawal of the end tab 254 of the retaining pin 250 from the slider 220 and retraction of the needle 16 ensures complete delivery of the dose of medicament. In one example, a time of 3 to 4 seconds elapses between the end tab 254 of the retaining pin 250 moving clear of the slider 220 and the link member 210 being decoupled from the slider 220, although a longer or shorter delay could be provided if desired.

FIG. 9(d) shows the device 100 once the needle 16 has been retracted. The compression spring 60 prevents further movement of the carriage 200 in the distal direction, so that the needle 16 remains positioned proximally with respect to the cover piece 304, inside the device 100. The device 100 can then be removed from the injection site, at which point the housing body 102 will move back to its initial position with respect to the chassis 300. The needle 16 remains hidden from view and shrouded within the device 100 after use, and the device 100 can be safely disposed of.

From the above, it will be understood that the retraction spring 60, the releasable coupling arrangement formed by the link member 210 and the slider 220, the crank assembly 270 and the constant force spring 80 together form a retraction mechanism for the device 100 that, after activation, moves the carriage in the proximal direction. Furthermore, the rotary damper defined by the rotor 282 and the chamber 284 of the crank assembly provide a time delay mechanism that creates a delay time between activation of the retraction mechanism, by withdrawal of the retaining pin 250 from the slider 220, and the start of movement of the carriage 200 in the proximal direction.

It will be appreciated that the device described with reference to FIGS. 1 to 9 includes several mechanisms that could be used independently or in different combinations in other devices, and that one or more of the mechanisms could be substituted with alternative arrangements as appropriate for a particular application.

For instance, alternative drive mechanisms for driving the stopper of the syringe could be employed. For example, the drive spring need not be arranged concentrically around a part of the array of balls. Instead, the drive member could be driven by one or more tension springs arranged alongside a part of the array of balls. For instance, in one variant (not shown), the drive member is driven by a pair of tension springs arranged on either side of the part of the array of balls on the right hand side of the carriage.

Figure 10:
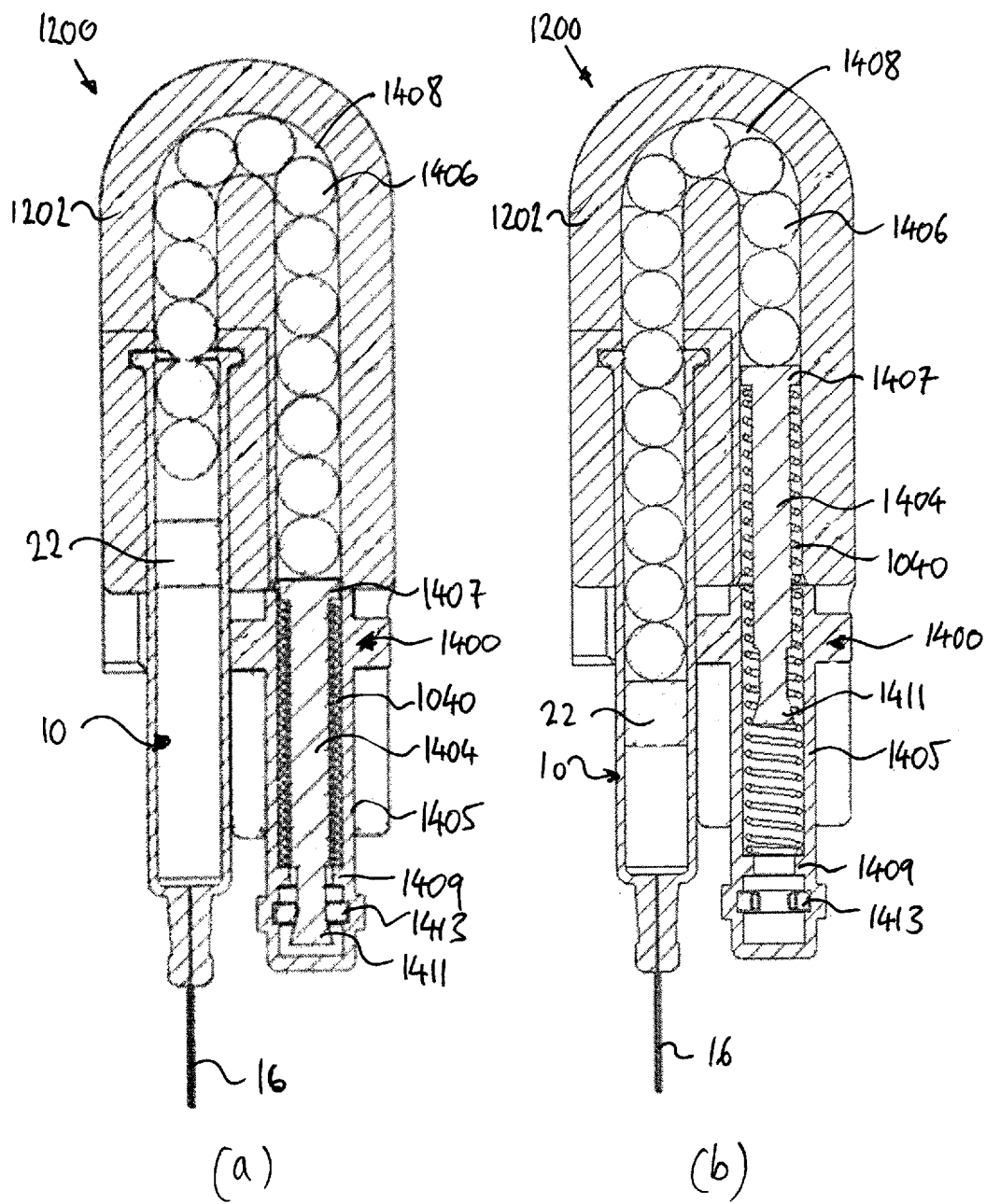

FIG. 10 is a schematic illustration of the carriage 1200 of another variant of the device in which the drive arrangement 1400 includes a compression spring 1040 for driving the piston member 1404, instead of a tension spring.

In the FIG. 10 variant, the carriage body 1202 is shaped to form the entire guide track 1408 for the balls. The piston member 1404 comprises an elongate rod housed within a piston housing part 1405 of the carriage body. The piston member has an enlarged-diameter head part 1407 at its proximal end, which acts as a spring seat for the proximal end of the compression spring 1040. The distal end of the compression spring 1040 bears against a collar 1409 formed in the bore of the piston housing 1405. The distal end 1411 of the piston member 1404 is frustoconically shaped for engagement with a pair of retaining pins 1413 that extend into the piston housing 1405.

In the initial state of the device, shown in FIG. 10(*a*), the piston member 1404 is held in its initial, latched position by the retaining pins 1413. During the operating sequence of the device, the pins 1413 are moved to release the piston member 1404, allowing the compression spring 1040 to drive the piston member 1404 in the proximal direction as shown in FIG. 10(*b*). The force of the spring 1040 is transferred to the stopper 22 of the syringe 10 by the array of balls 1406, as in the example described above with reference to FIGS. 1 to 9.

Although not shown in FIG. 10, it will be appreciated that the carriage 1200 can be used in a device having some or all of the features of the device 100 described with reference to FIGS. 1 to 9. For example, the carriage 1200 may be provided with features including a carriage latch arrangement for latching the carriage 1200 in position with respect to a chassis, a releasable coupling arrangement for coupling the carriage to an insertion spring, a sprocket arrangement for activating the coupling arrangement, a viscous damping arrangement for delaying the decoupling of the insertion spring, and a cavity for engagement with a retraction spring. It will also be appreciated that the retaining pins can be released by relative movement of the carriage 1200 with respect to other components of the device, for example by cooperation with a trigger pin attached to a chassis or by any other suitable arrangement upon movement of the carriage in a needle insertion direction.

Figure 11:
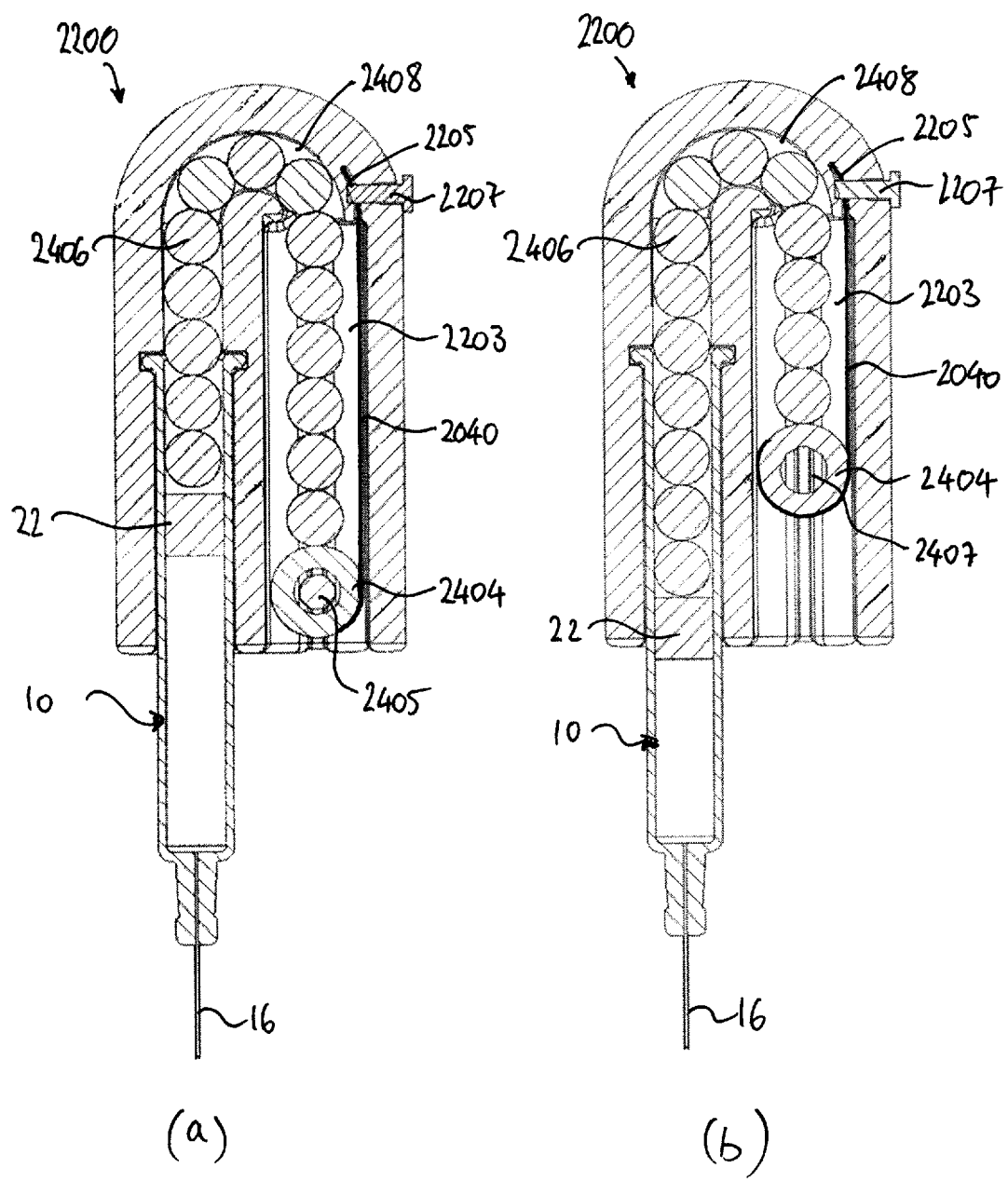

FIG. 11 shows, schematically, a carriage 2200 having another alternative drive arrangement 2400, in which a constant force spring 2040 is used to drive movement of the plunger member 2404. In this case, the linear, right hand side part of the guide track 2408 for the balls 2406 is intersected by a slot 2203 that extends within the carriage body 2202. The plunger member 2404 is ring-shaped and is accommodated in and guided for linear movement by the slot 2203. One end of the constant force spring 2040 is anchored on the circumference of the plunger member 2404, and the other end of the constant force spring 2040 is retained in a slit 2205 in the carriage body by a pin 2207 that extends laterally into the slit 2205.

In the initial state of the device, shown in FIG. 11(*a*), the plunger member 2404 is retained at the distal end of the slot 2203 by a retaining pin 2405, which engages with the central aperture 2407 of the plunger member 2404.

During the operating sequence of the device, the retaining pin 2405 is caused to out of engagement with the plunger member 2404, for example due to relative movement between the carriage 2200 and the housing and chassis of the device. Relaxation of the constant force spring 2040 causes the plunger member 2404 to move proximally along the slot 2203 as shown in FIG. 11(*b*). In this way, the force of the spring 2040 is transferred to the stopper 22 of the syringe 10 by way of the array of balls 2406. Again, the carriage 2200 shown in FIG. 11 could be used in a device having some or all of the features of the device of FIGS. 1 to 9.

Other drive arrangements are also possible. For example, it is conceivable that the sprocket could be driven by a driving element, such as a power spring, to apply a drive force to the balls. In this way, the sprocket comprises the drive member.

Common to all of the above-described arrangements is the provision of an array of balls to transmit force from the piston member to the stopper of the syringe. Preferably, the balls are metal ball bearings, which allow transmission of the force with minimal flexing or elastic deformation. However, it is conceivable that other force transmission means could be provided. For example, a flexible plastic rod, a close-wound spring, a link chain or any other suitable arrangement could be used. It is also possible that the force transmission means could be integral with or fixed to the piston member.

In the illustrated examples, the drive axis along which the piston member moves is parallel to and spaced from the axis of the container, along which the stopper moves to expel the medicament. The piston member is disposed alongside the container, and the piston member and the stopper move in opposite directions relative to the carriage. Thus, the force transmission means serves to redirect the force of the drive spring through 180 degrees. This results in a relatively compact arrangement. However, other arrangements of the components within the carriage are possible, including those in which the drive axis and the container axis are non-parallel. It is also conceivable that the drive axis and the container axis could be coaxial, so that the drive mechanism is arranged coaxially with the container. In this case, the force transmission means would not change the direction of the driving force.

In the illustrated embodiments, the carriage moves in the distal direction with respect to the chassis to insert the needle and in the proximal direction to withdraw the needle. However, other arrangements are possible, and in general terms the carriage is movable with respect to the chassis in an insertion direction to insert the needle, and in a retraction direction that is opposite to the insertion direction to withdraw and shroud the needle.

The use of a rotary damper provides a compact and predicable means for introducing a delay time between activation of the retraction mechanism and the retraction movement of the carriage. Preferably, the damping fluid is selected such that the viscosity of the damping fluid is not substantially changed over the range of temperatures in which the device might be expected to be used, which may include use straight after removal of the device from a refrigerator and/or use of the device in relatively hot environmental conditions.

Other time delay mechanisms could be used. For example, instead of a rotary damper, a linear viscous damper or other damping arrangement could be used. It is also conceivable that an escapement mechanism, gear train or other mechanical delay arrangement could be used. It will also be appreciated that, in some applications, a time delay mechanism may not be required, in which case the insertion spring could be decoupled from the carriage substantially immediately upon activation of the retraction mechanism.

In some further applications, the retraction mechanism could be omitted, and the needle could be withdrawn manually after delivery of the medicament. The device described with reference to FIGS. 1 to 9 has an interlock arrangement in which the housing body acts as an interlock member and can be moved relative to the chassis of the device to switch the device from a neutral state to a ready state. It will be appreciated that an alternative interlock arrangement could be used. In particular, the interlock member need not form part of the housing of the device, but could take the form of a separate component that is arranged to move with respect to the chassis when the device is placed against the skin. Devices without an interlock arrangement are also possible.

In the illustrated examples, a pre-filled syringe having staked needle is used to contain the medicament. It is also possible that a container with a separate attachable needle could be used. For example, the container could be a cartridge-type vial. It is also conceivable that, in place of a hypodermic needle, a different type of cannula or other means for delivery of the medicament could be used.

Further modifications and variations of the examples described above are also possible without departing from the scope of the invention as defined in the appended claims.

The invention claimed is:

1. A medicament delivery device for a delivery of a medicament from a container through a cannula, the container having a stopper for containing the medicament within the container, the device comprising:
a chassis;
a carriage for retaining the container and the cannula;
an insertion spring for biasing the carriage for movement in an insertion direction with respect to the chassis from a starting position in which the cannula is shrouded to an insertion position in which the cannula is extended; and
a drive mechanism for driving the stopper along a container axis to expel the medicament through the cannula upon activation of the drive mechanism;
wherein the drive mechanism is carried by the carriage and comprises a drive member that is movable with respect to the carriage, a drive means for applying a driving force to the drive member along a drive axis, and a force transmission means comprising a non-deformable element for transmitting the driving force from the drive member to the stopper; and
wherein the drive means comprises a tension spring, wherein the tension spring circumferentially surrounds the non-deformable element.

2. The medicament delivery device according to claim 1, wherein the drive means comprises a first end coupled to the drive member and a second end coupled to the carriage, and wherein the force transmission means is disposed at least partly between the first end and the second ends of the drive means.

3. The medicament delivery device according to claim 1, wherein the drive axis is parallel to and spaced from the container axis.

4. The medicament delivery device according to claim 3, wherein the drive means is disposed alongside the container.

5. The medicament delivery device according to claim 1, wherein the force transmission means comprises an array of balls.

6. The medicament delivery device according to claim 1, wherein a first end of the force transmission means is aligned with the drive axis, and wherein a second end of the force transmission means is aligned with the container axis.

7. The medicament delivery device according to claim 1, wherein a part of the force transmission means is received or receivable in the container.

8. The medicament delivery device according to claim 1, wherein the force transmission means is guided in a guide track associated with the carriage.

9. The medicament delivery device according to claim 1, wherein the drive mechanism comprises a guide element for guiding movement of the drive member along the drive axis, and wherein the tension spring is arranged concentrically around the guide element.

10. The medicament delivery device according to claim 9, wherein
the force transmission means is guided in a guide track associated with the carriage; and
the guide track is defined in part by the guide element.

11. The medicament delivery device according to claim 9, wherein the guide element is generally tubular.

12. The medicament delivery device according to claim 11, wherein the drive member comprises a guide formation for cooperation with a slot in the guide element to prevent turning movement of the drive member.

13. The medicament delivery device according to claim 1, further comprising a shock absorber disposed between the drive member and the stopper.

14. The medicament delivery device according to claim 1, wherein the drive mechanism is activated in response to the carriage reaching an activation position during the movement of the carriage towards the insertion position.

15. The medicament delivery device according to claim 14, comprising a drive trigger for activating the drive mechanism when the carriage reaches the activation position.

16. The medicament delivery device according to claim 15, wherein the drive trigger is associated with the chassis.

17. The medicament delivery device according to claim 15, wherein the drive mechanism comprises a drive latch for latching the drive member in an initial position, and wherein the drive trigger is arranged to cooperate with the drive latch when the carriage reaches the activation position to release the drive member for movement along the drive axis.

18. The medicament delivery device according to claim 17, comprising a latch stop associated with the carriage and wherein the drive latch is arranged to engage with the latch stop to hold the drive member in the initial position.

19. The medicament delivery device according to claim 18, comprising a spring means for biasing the drive latch into engagement with the latch stop.

20. The medicament delivery device according to claim 1, comprising a carriage latch arrangement for holding the carriage in the starting position and for allowing the movement of the carriage in the insertion direction under a bias of the insertion spring upon release of the carriage latch arrangement.

21. The medicament delivery device according to claim 20, comprising a trigger component operable to release the carriage latch arrangement.

22. The medicament delivery device according to claim 21, comprising an interlock member and an interlock spring for biasing the interlock member and the chassis apart, wherein the interlock member is movable with respect to the chassis against a bias of the interlock spring to switch the device from a neutral state in which release of the carriage latch arrangement is not possible to a ready state in which the trigger component is operable to release the carriage latch arrangement.

23. The medicament delivery device according to claim 22, wherein the interlock member comprises a housing body for retaining the trigger component.

24. The medicament delivery device according to claim 1, wherein the insertion spring is disposed parallel to and spaced from both the drive axis and the container axis.

25. The medicament delivery device according to claim 1, wherein the insertion spring comprises a tension spring.

26. The medicament delivery device according to claim 25, further comprising a coupling mechanism for releasably coupling the insertion spring to the carriage, wherein the drive mechanism is arranged to activate the coupling mechanism to cause decoupling of the insertion spring from the carriage after delivery of the medicament, thereby to allow movement of the carriage away from the insertion position.

27. The medicament delivery device according to claim 1, further comprising a retraction spring for driving movement of the carriage away from the insertion position to retract the cannula after delivery of the medicament.

* * * * *